US012582287B2

(12) United States Patent
Rusoke-Dierich

(10) Patent No.: US 12,582,287 B2
(45) Date of Patent: Mar. 24, 2026

(54) MEDICAL DEVICE, ACCESSORIES FOR USE THEREWITH, AND METHODS OF USE

(71) Applicant: JD Sanmed Medical Technology Pty Ltd, Brisbane (AU)

(72) Inventor: Olaf Rusoke-Dierich, Douglas (AU)

(73) Assignee: JD Sanmed Medical Technology Pty Ltd, Brisbane City (AU)

( * ) Notice: Subject to any disclaimer, the term of this patent is extended or adjusted under 35 U.S.C. 154(b) by 1072 days.

(21) Appl. No.: 17/045,043

(22) PCT Filed: Apr. 5, 2019

(86) PCT No.: PCT/AU2019/050306
§ 371 (c)(1),
(2) Date: Oct. 2, 2020

(87) PCT Pub. No.: WO2019/191818
PCT Pub. Date: Oct. 10, 2019

(65) Prior Publication Data
US 2021/0145251 A1     May 20, 2021

(30) Foreign Application Priority Data

Apr. 5, 2018     (AU) ................................ 2018901129

(51) Int. Cl.
*A61B 1/018*          (2006.01)
*A61B 1/00*           (2006.01)
(Continued)

(52) U.S. Cl.
CPC ...... *A61B 1/00011* (2013.01); *A61B 1/00045* (2013.01); *A61B 1/00121* (2013.01);
(Continued)

(58) Field of Classification Search
CPC ............ A61B 1/00011; A61B 1/00045; A61B 1/00121; A61B 1/00128; A61B 1/0014;
(Continued)

(56) References Cited

U.S. PATENT DOCUMENTS 4,006,738 A * 2/1977 Moore ..................... A61B 1/07
                                                    385/119
5,026,368 A * 6/1991 Adair ................... A61B 5/0071
                                                    606/15

(Continued)

FOREIGN PATENT DOCUMENTS

CN          201806688 U       4/2011
CN          106176041        12/2016
(Continued)

OTHER PUBLICATIONS

International Search Report for PCT/AU2019/050306, mailed Jun. 21, 2019, 6 pages.
(Continued)

*Primary Examiner* — Travis S Fissel
(74) *Attorney, Agent, or Firm* — Nixon & Vanderhye PC

(57) ABSTRACT

The present invention is directed to a medical device (521) for inspecting and/or accessing a patient, the device including: a base (520); an image capturing device for capturing images of the patient (541), the image capturing device being located in the base; means to communicate the captured image to a display for displaying said captured image; wherein the base includes one or more openings (525) through which the patient is able to be directly inspected, the one or more openings being located around the image capturing device (541).

22 Claims, 15 Drawing Sheets

(51) Int. Cl.

| | | |
|---|---|---|
| *A61B 1/06* | (2006.01) | |
| *A61B 1/227* | (2006.01) | |
| *A61B 1/267* | (2006.01) | |
| *A61B 1/31* | (2006.01) | |
| *A61B 5/00* | (2006.01) | |
| *G03B 13/04* | (2021.01) | |
| *G03B 15/14* | (2021.01) | |

(52) U.S. Cl.

CPC ........ *A61B 1/00128* (2013.01); *A61B 1/0014* (2013.01); *A61B 1/018* (2013.01); *A61B 1/06* (2013.01); *A61B 1/227* (2013.01); *A61B 1/267* (2013.01); *A61B 1/31* (2013.01); *A61B 5/0077* (2013.01); *G03B 15/14* (2013.01); *G03B 13/04* (2013.01)

(58) Field of Classification Search

CPC ........... A61B 1/018; A61B 1/06; A61B 1/227; A61B 1/267; A61B 1/31; A61B 1/015; A61B 1/00105; A61B 1/00195; A61B 1/042; A61B 1/0607; A61B 1/04; A61B 1/053; A61B 1/07; A61B 5/0077; A61B 5/445; A61B 3/10; A61B 3/14; A61B 3/145; A61B 2090/502; G03B 15/14; G03B 15/04

USPC ......... 351/206; 600/184–185, 188, 199–200, 600/227–228, 235–236, 245–246, 109, 600/112, 122; 348/77–78

See application file for complete search history.

(56) References Cited

U.S. PATENT DOCUMENTS

| | | | |
|---|---|---|---|
| 5,239,984 A | | 8/1993 | Cane et al. |
| 5,599,276 A | | 2/1997 | Hauptli et al. |
| 5,665,094 A | | 9/1997 | Goldenberg |
| 5,762,605 A | | 6/1998 | Cane et al. |
| 7,354,399 B2 * | | 4/2008 | Strom ................... A61B 1/227 |
| | | | 600/200 |
| 2001/0000672 A1 * | | 5/2001 | Ooshima ........... A61B 1/00177 |
| | | | 348/65 |
| 2003/0171655 A1 * | | 9/2003 | Newman ............... A61B 1/227 |
| | | | 600/200 |
| 2004/0189799 A1 | | 9/2004 | Spencer |
| 2005/0200707 A1 | | 9/2005 | Yogesan |
| 2012/0081593 A1 | | 4/2012 | Nakagawa et al. |
| 2013/0209954 A1 | | 8/2013 | Prakash et al. |
| 2013/0271589 A1 | | 10/2013 | Huang |
| 2015/0018621 A1 | | 1/2015 | Wellen |
| 2016/0209727 A1 | | 7/2016 | Smith et al. |
| 2017/0071509 A1 * | | 3/2017 | Pandey ............... A61B 5/0075 |

FOREIGN PATENT DOCUMENTS

| | | |
|---|---|---|
| JP | 2005274972 | 10/2005 |
| JP | 2007/324976 | 12/2007 |
| WO | 2004/080062 | 9/2004 |

OTHER PUBLICATIONS

Written Opinion of the ISA for PCT/AU2019/050306, mailed Jun. 21, 2019, 9 pages.

Search Report for AU2018901129, mailed Oct. 19, 2018, 18 pages.

Extended European Search Report issued in European Application No. 19781989.9 dated Nov. 11, 2021 (7 pages).

Office Action dated Jul. 16, 2024 in EP counterpart application No. 19781989.9 (see global dossier).

* cited by examiner 111
120
130
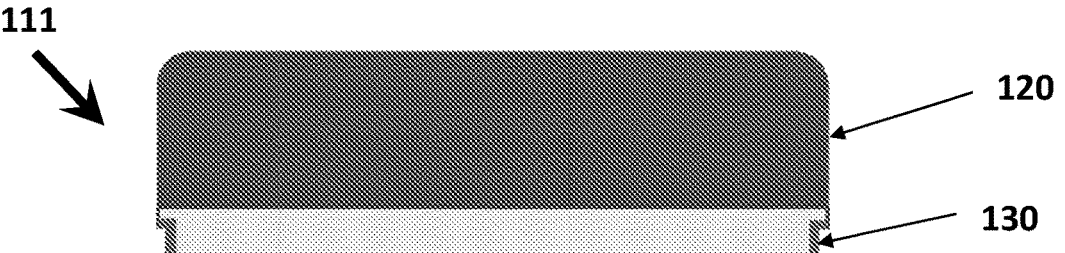
FIG 2A
143
125
124
130
131
141
127
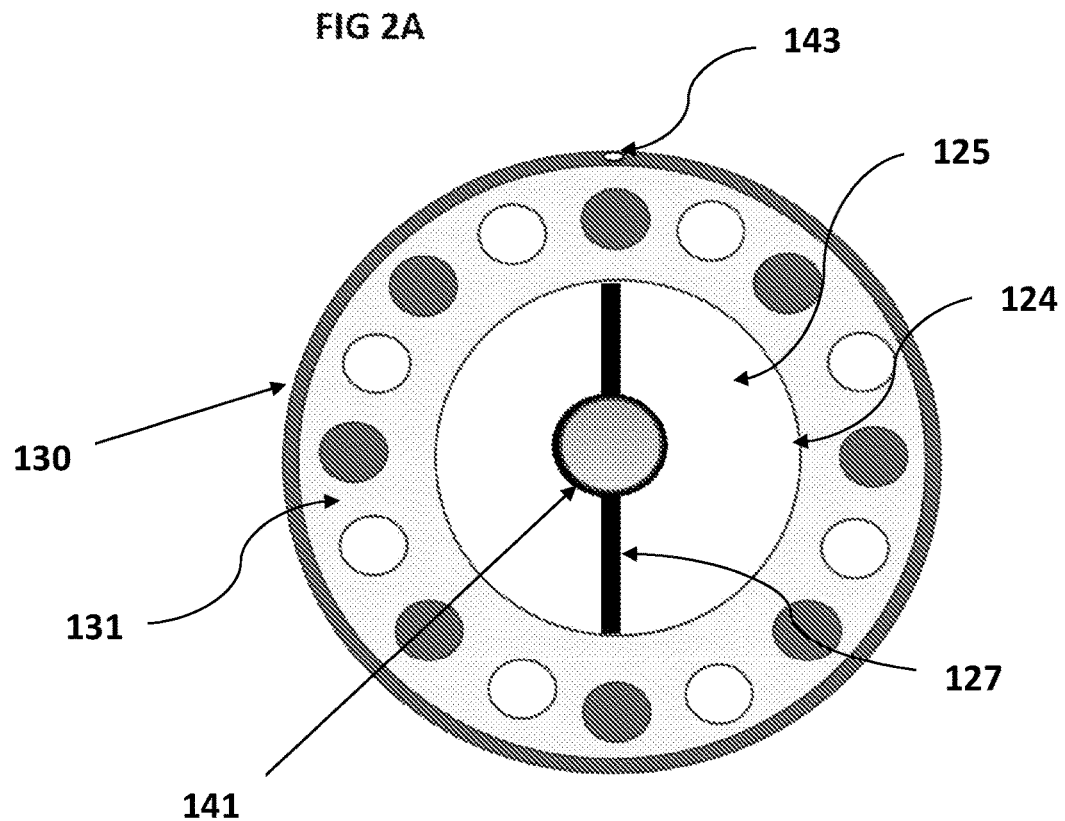
FIG 2B
141
142
127
143
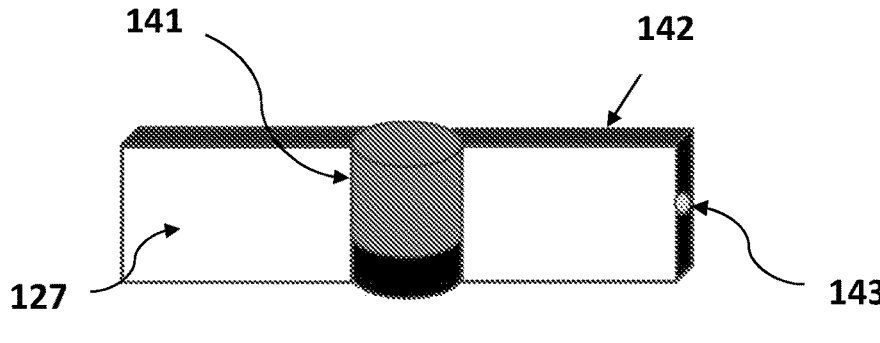
FIG 2C

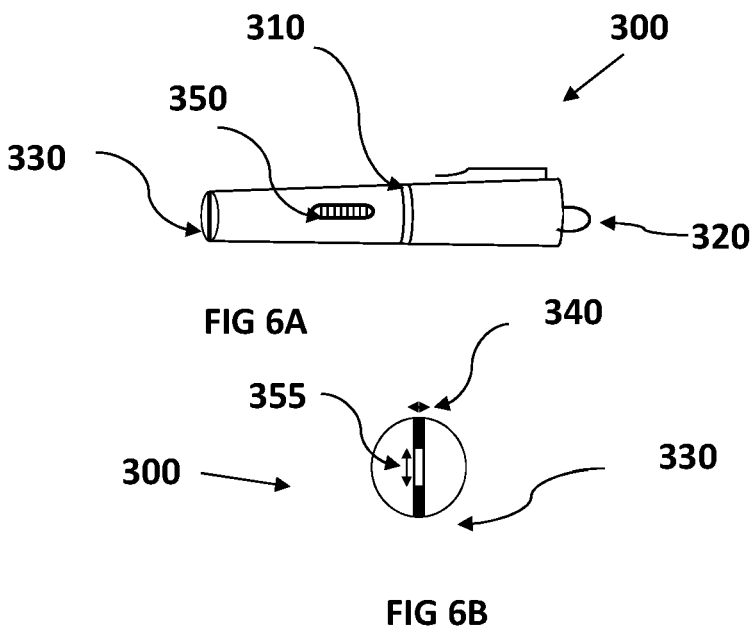
FIG 6A
FIG 6B
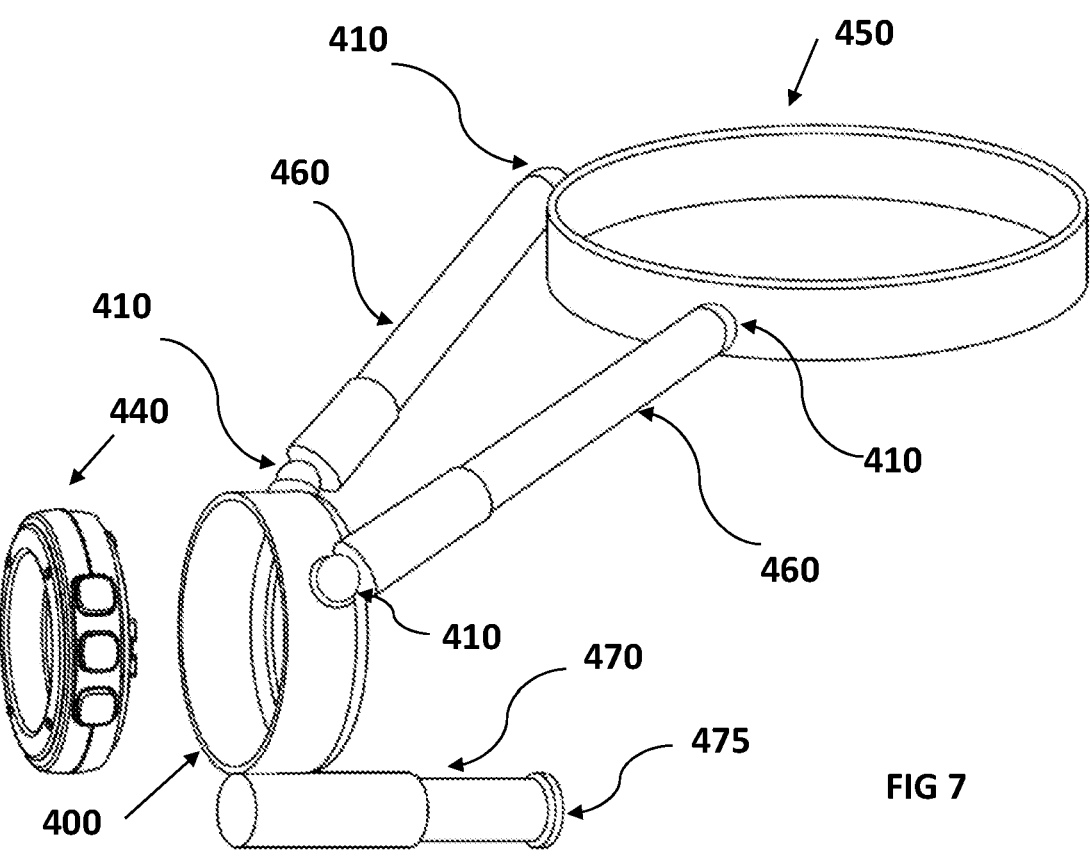
FIG 7

535

570

550

540

554

521

520

550

520

520

521

541

525

532

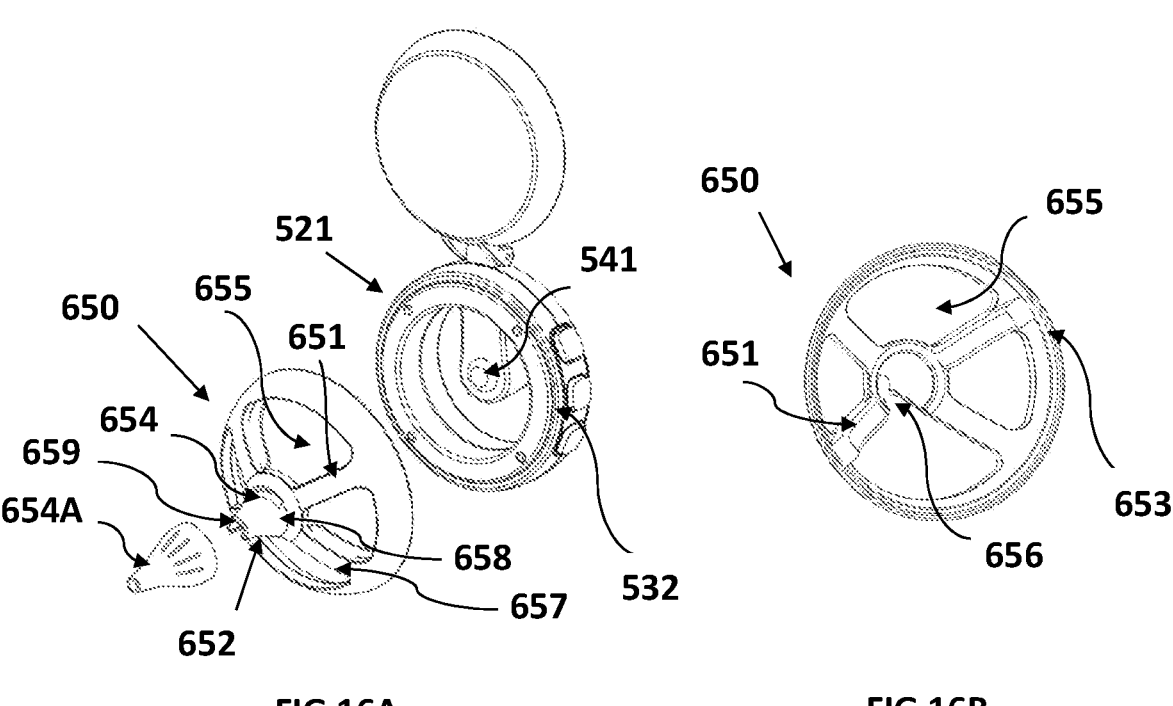
FIG 16A                    FIG 16B
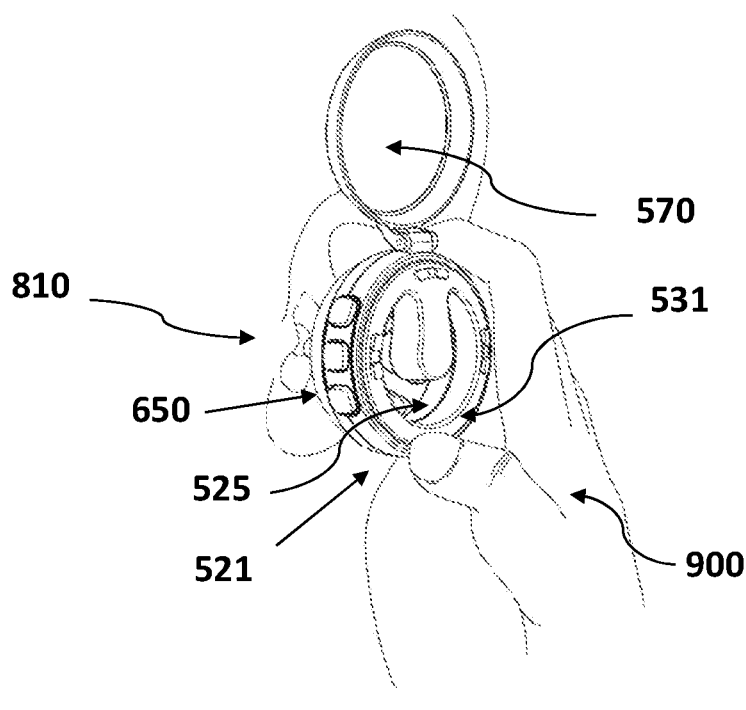
FIG 17

MEDICAL DEVICE, ACCESSORIES FOR USE THEREWITH, AND METHODS OF USE

This application is the U.S. national phase of International Application No. PCT/AU2019/050306 filed 5 Apr. 2019, which designated the U.S. and claims priority to AU patent application No. 2018901129 filed 5 Apr. 2018, the entire contents of each of which are hereby incorporated by reference.

TECHNICAL FIELD

The invention relates to medical devices, and in particular, the invention relates to devices for medically inspecting or accessing a patient, where the inspection or access is part of examining and/or performing an operation and/or a procedure on a patient. The invention also relates to devices for use in the performance of operations or procedures on a patient. The invention is particularly related to devices for optically enabled medical inspection, medical operations or medical procedures, however, it will be appreciated that the invention is not limited to those particular fields of use.

BACKGROUND ART

In medical practice, especially in general practice, practitioners may have familiarity with a variety of medical devices for use during a consultation with a patient. Devices may include an otoscope (for examining, or performing procedures or operations on the ear), an ophthalmoscope (for examining the exterior of the eye, also called a slit lamp; and for examining the interior of the eye, also referred to as a fundoscope) or other devices used for eye examination and/or operation, a dermatoscope (for examining the skin) or an oroscope (for examining the mouth).

Traditionally, medical inspection devices such as those mentioned above incorporate simple optical parts such as a lens and a light to enlarge and illuminate the inspected area. Typically, such devices include a stem for handling the device, the stem including a compartment for receiving rechargeable or disposable batteries. In the case of multiple purpose scopes, there may be a connection point to connect with, for example, an otoscope, a dermatoscope (also called a dermascope) or an oroscope.

There may also be different varieties of scopes within each class of scope. For example, some otoscopes have a sealed or airtight head which permits pneumatic use of the otoscope for specific diagnostic applications (e.g. diagnosis of middle ear infection with effusion).

Other otoscopes, particularly those used by Ear, Nose and Throat (ENT) specialists, are differently designed. These otoscopes have an open speculum for insertion into the ear tube which permits operations or procedures to be performed through the specula. The specula of these devices may be reusable, and magnification is often performed by the use of magnifying glasses or binoculars worn by the practitioner or by using an ear microscope. When using magnifying glasses or binoculars, a light source providing light into the specula may interfere with the view of the practitioner. The use of an ear microscope allows good magnification and light source, but the instrument itself may be expensive and require detailed training to be used appropriately.

In relation to eye examination, the fundoscope is commonly used to inspect the cornea, or the back of the eye (retina), and the quality of examination depends on the experience of the practitioner with the device he or she is using. In addition, to use the ophthalmoscope the practitioner may need to be in close proximity to the patient, and this can sometimes be a cause for discomfort in the practitioner and/or patient.

Other devices used in relation to the eye include a slit-lamp which is commonly used by eye specialists (ophthalmologists) or in emergency departments to examine the entire eye, the anterior chamber, the lens or the eyelids, or to remove foreign bodies, or assess the corneal damage of an eye by performing fluorescein examination. This device is very bulky and hand to eye co-ordination during procedures and/or operations is difficult to maintain as the practitioner must look through a lens to examine the eye of the patient, but at the same time the practitioner must move the device into the appropriate location to perform the examination.

Some newer devices include a camera and digital display, such that the practitioner looks exclusively at the display in real-time video (or still images) to conduct the inspection. These devices provide numerous advantages over their more traditional counterparts, including by providing clear evidence to assist medico-legal queries, collaborative assessment via image sharing, and making the assessment less subjective by removing reliance on language alone to communicate a practitioner's findings.

However, these devices hinder the ability for the practitioner to coordinate movement of the device relative to the patient because the display blocks a direct view of the patient.

Therefore, existing devices have been lacking in one or more respects including but not limited to:

- a) Many of the devices are bulky or not easy to hold or manipulate, as may take up substantial space in the medical suite of the practitioner;
- b) some devices may not provide an adequate view for the practitioner, including by having a view adversely effected by an external light source or not providing sufficient magnification;
- c) some devices do not provide for adequate access to the patient, as the bulk of the device blocks the access to the patient that the practitioner needs to perform procedures or operations on a patient.
- d) many devices are prohibitively expensive for the average practitioner;
- e) some devices may be awkward or uncomfortable to use;
- f) many devices provide for disconnected visual and motor co-ordination during examination and/or operation, particularly because they do not provide a direct line of sight of the patient; and
- g) newer devices with digital image capturing technology may not give the practitioner the desired freedom to store and move the images captured by the device, or they can inhibit access to the patient during an operation or procedure.

It may therefore be beneficial for medical devices used for inspecting a patient, whether that be examining and/or operating and/or performing procedures on a patient, to be appropriately sized, easy to handle, provide for high quality inspection without requiring an understanding of idiosyncratic techniques, and be of reasonable cost. It may additionally be helpful for the device to include a camera or other means to record images for easy access and sharing with relevant parties.

It is to be understood that, if any prior art information is referred to herein, such reference does not constitute an admission that the information forms part of the common general knowledge in the art, in Australia or any other country.

SUMMARY OF INVENTION

The present invention arises from a recognition that improvements in medical devices used for examining and/or operating and/or performing procedures on a patient can be achieved by a medical device which addresses one or more of the shortcomings of the prior art, or at least provides a useful alternative thereto.

According to one aspect of the invention, there is provided a medical device for inspecting a patient, the device including:

a base;

an image capturing device for capturing images of the patient; and means to communicate the captured image to a display for displaying said captured images;

wherein the base includes one or more openings through which the patient is able to be directly inspected, the one or more openings being located around the image capturing device.

Preferably, the image capturing device is located in the base.

Preferably, the one or more openings are adapted to provide direct access to the patient through the one or more openings. Preferably the ability for the device to provide direct access to the patient permits the performance of procedures and/or operations through the one or more openings.

Preferably, the one or more openings surround, or substantially surround, the image capturing device.

In a particularly preferred form, the image capturing device is embedded in the base.

There may be a plurality of image capturing devices. Preferably, the plurality of image capturing devices are located in, or embedded in, the base.

A medical device according to any one of the preceding claims, wherein the display is located adjacent to the one or more openings.

In a preferred form, the image capturing device, or at least one of the plurality of image capturing devices, is able to capture images of the parts of the patient that are directly viewable through the one or more openings of the base.

The device preferably provides for a first and a second inspection of a patient, whereby the first inspection is by direct inspection of the patient through the one or more openings, and the second inspection is by inspection of the images of the patient captured by the image capturing device on the display.

Preferably, the first and second inspections are able performed contemporaneously.

It is preferred that the same, or substantially the same, part of the patient is contemporaneously viewable by the first inspection and the second inspection.

The device may also provide for a third inspection to be conducted at some time after the inspection has been conducted, either during a review of the inspection by the medical practitioner that performed the inspection, or by another medical practitioner advising in relation to the patient.

The display may be located on the device. Preferably, the device includes a lid and the display is located on a lid of the device. The lid may be movable relative to the base of the device, from an open position to a closed position, and vice versa. Preferably, when the lid is in the open position, the patient is directly viewable or accessible through the medical device. The lid is preferably able to be pivotably moved relative to the base of the device. When the lid is in a closed position it covers an upper surface of the base device. Preferably, the lid is shaped such that when it is closed it covers substantially the whole upper surface of the medical device.

The base preferably includes a peripheral portion. In a preferred form the one or more openings are preferably located between the image capturing device and the peripheral portion. One or more of the openings may be located in the peripheral portion itself.

In a preferred form, the image capturing device is located within the peripheral portion. In an alternative preferred form, the image capturing device(s) may be located on the peripheral portion itself.

The peripheral portion may be ring shaped, oval shaped, polygon shaped, and more particularly convex polygon shaped. The peripheral portion may be rectangular or square shaped.

The image capturing device (or at least an external facing part thereof) is preferably located in a lower surface of the base device.

The image capturing device, or at least one of the plurality of image capturing devices, may be located centrally within the peripheral portion. The image capturing device may alternatively be located towards an inner edge of the peripheral portion. As a further alternative, the image capturing device may be located generally within the peripheral portion (i.e. within the perimeter of, but not part of, the peripheral portion itself). Depending on the shape of the base, there may be provided image capturing device(s) one or more of the different locations of the base set out herein.

The image capturing device may be located within a first a plane defined by an upper surface of the peripheral portion, and a second a plane defined by a lower surface of the peripheral portion. Preferably, a lower extremity of the image capturing device is located in the second plane defined by the lower surface of the peripheral portion.

One or more struts may be used to locate the image capturing device within the peripheral portion. The one or more struts may extend inwardly from the peripheral portion to the image capturing device. There may be four struts extending from the image capturing device in a cross formation. Where there is a plurality of image capturing devices, there may be at least one located on a strut extending inwardly from the peripheral portion, and at least one image capturing device located on the peripheral portion of the base of the device.

The image capturing device and/or strut may be located in an elevated position with respect to upper surface of the peripheral portion of medical device (i.e. the image capturing device and/or strut is closer to the medical examiner than the upper surface of the peripheral portion).

The device may include one or more struts that extend upwardly from the peripheral portion of the base to locate the image capturing device, or at least one of the plurality of image capturing devices, in an area above the one or more openings of the base.

Preferably the image capturing device, or at least one of the plurality of image capturing devices, is located in a central axis of the device when the device is viewed in plan.

In a particularly preferred embodiment, the image capturing device is centrally located on a single strut that extends upwardly from the peripheral portion of the base. The single strut preferably extends into the area above the one or more opening(s) of the base. Preferably, the form of the strut and the location of the camera provide improved inspection and/or access to the medical practitioner when the device is used for examining and/or performing a procedure or operation on the patient. In a further particularly preferred form, the base of the device includes a substantially cylindrical single opening (i.e. the opening is circular when the base is viewed in plan view).

The device is preferably able to be handled by the thumb and one or more finger by a person (i.e. medical practitioner) for inspecting the patient. The device is preferably able to be handled by the peripheral portion. The device is preferably able to be handled by the one or more struts.

The device may include a removable protective cover for protecting the lower surface of the base device, including the lens(es) of the one or more image capturing devices and/or the light sources. The protective cover may be shaped to closely fit part of the lower surface of the base device. The cover may be rounded or smooth for increased patient comfort. The cover may be made of glass, plastic and be sterilisable so that it may be hygienically reused after contacting patients. The projective cover may be disposable.

The image capturing device(s) may be able to rotate, swivel, turn or otherwise be moved with respect to the base of the device. The movement of the image capturing device (s) may preferably be controlled by a user operating one or more controls located on the device (the controls are described elsewhere in the specification, but may include voice activated control or control by a touchpad or buttons).

Preferably, the image capturing device is a digital camera. The image capturing device may include a CMOS, sCMOS or CCD digital sensor, or other appropriate digital sensors known to the person skilled in the art.

Preferably, the image capturing device is able to provide controllable zooming. The zooming may be digital and/or optical zooming.

The images captured by the image capturing device preferably include still frames or video footage.

Preferably, the image capturing device is able to take image snapshots during the course of capturing a digital video recording.

Preferably, the device includes data storage means to store the images captured by the image capturing device on the device itself. The data storage means is preferably a digital machine readable medium capable of receiving data from, and storing in a digitally readable format the images captured by, the image capturing device.

The communication means to communicate images captured by the image capturing device to the display is also able to communicate said captured images to storage means on the device or another computing device (e.g. the medical practitioner's computer, tablet, mobile phone, etc., and/or a computer or server of the institution in which the medical practitioner provides medical treatment). The communications means may communicate the images captured by the image capturing device to a display for contemporaneous inspection by the medical practitioner without recording those images in a format that can later be reproduced, though in many contexts this may be desirable, and the device is therefore configurable to make such recordings.

The communication means may include a Bluetooth connection, or other technologies implementing wireless communication standards or protocols, and in particular those technologies known to the person skilled in the art of short or long range communication applications in patient monitoring, control or diagnostics. Alternatively, the communication means may be over a Wi-Fi network or another wireless LAN network, by USB cable or by other display connectors such as HDMI or MHL standard cable, mini-VGA, RF connector or mini-DVI connector.

Preferably, the device is able to be controlled and/or the data stored on the device is able to be managed by a secure software application. The secure software application may comprise a mobile telephone/tablet/other personal device application or personal computer program which is accessible by the medical practitioner or other authorised persons only.

The display may be built into the device, or a separate smartphone screen, desktop screen or other screen such as tablet or smartwatch. The display preferably shows settings of the image capturing device in in addition to the captured image. The display may be located on the lid of the device in a preferred form of the invention.

The display is preferably a touchscreen, which includes the ability to both present the images captured by the image capturing device, as well as provide other controls or functions for the user of the device. In particular, it is preferred that a touchscreen display is provided on the device itself. Preferably, the touchscreen display is located on a surface of the lid of the device. In a particularly preferred form, the touchscreen display is located on side of the lid which faces the base of the device when the lid is in a closed position.

Preferably, where the display is not integral or built into the device, the display is locatable proximate to the base. The display may be locatable proximate to an opening of the base. The display may be attachable to a person via an attachment clip. The display may be attachable to a wrist of the person.

The display may alternatively be locatable remotely from the base in use, preferably where there is no disruption to the practitioner's view of or access to the patient (e.g. the display is located on a wall directly behind where a patient is sitting). The display may be mountable to a surface or to a computer screen.

The device is preferably suitable for performing examinations of and/or operations and/or procedures on the patient. Preferably, the examinations, operations and/or procedures are able to be performed through or with the assistance of the openings in the device and/or adaptors or other components connected to the base device as described herein.

The medical device preferably includes at least one light source for illuminating the patient for inspection. The at least one light source may be located on a lower surface of the base. The at least one light source may include a combination of blue and white light sources, or a combination of other colour light sources. In particular, the at least one light source may include a green light source. The green light source may be particularly suitable for use when the device is used as an ophthalmoscope (e.g. to view the foveal reflex). Preferably, the base device provides non-polarised and/or polarised coloured or white light. The intensity of the at least one light source may be controllable. Preferably, one set of coloured lights may be independently controllable from a second set of differently coloured lights.

The medical device preferably includes optics such as a lens or another optical component such as a mirror, polarizer or optical filter. The optics may be controllable to provide a variety of magnification or viewing settings, depending on the combination of the optical components used and the how they are controlled.

The image capturing device can preferably take unmagnified or 'normal' pictures of the patient so that entire body parts may be captured in the image (e.g. the back or the arm).

The unmagnified images can provide a larger view of the patient so that the context of a medically relevant attribute or condition may be captured. For example, where the medical practitioner is documenting moles or skin lesions, a mole or lesion to be excised may be marked using the software used to show the image on the display. The unmagnified image including the marked mole or lesion may help the location of that mole or lesion when the patient returns for a subsequent inspection (i.e. a subsequent examination, operation or procedure).

The peripheral portion may include one or more bulging portions. A bulging portion may house one or more image capturing devices and/or one or more light source(s). The one or more bulging portion(s) preferably bulge towards the centre of an opening of the base device (or the one or more centres of the openings of the base device, respectively).

The medical device includes one or more controls. The controls may include one or more buttons, control wheels, a touchscreen and/or a touchpad. The one or more controls may be able to control one or more of: the one or more light sources; the image capturing device; the display; the image capturing device(s); optics in the device and/or the means for communicating or storing the captured images.

The controls are preferably located on an outer surface of the base. The controls may be located on the upper outer surface of the base. The controls may alternatively be located elsewhere, including on other locations on the base (e.g. on an outer peripheral side wall of the base), the lid or on the display. The one or more controls may be operated by voice and/or touch activation (e.g. in combination with a display including a touchscreen). Preferably, one of the controls comprises a scroll wheel provided on the upper surface or side of the base device. In a particularly preferred form, the scroll wheel is adapted to control the zooming in or out of image captured by the image capturing device.

In a particularly preferred form, one of the controls may comprise a touchscreen located on the interior surface of the lid and/or a scroll wheel provided on the upper surface or side wall of the base device. Preferably, in addition to being able to display the captured image, the touchscreen is able to display functions and settings for controlling image capturing device and/or communicating the captured images.

Preferably the base device is shaped such that it may held by a single hand of the medical practitioner, where said single hand can operate at least one of the controls. Preferably, the medical practitioner can simultaneously operate the touchscreen by a first digit on the single hand of the practitioner holding the device and/or operate the scroll wheel by a second digit on the single hand of the practitioner holding the device. In this way the device can be held by other digits on said single hand of medical practitioner, while he or she simultaneously uses a first and/or second digit on the same hand to control a touchscreen or scroll wheel of the device.

Preferably, there are provided one or more grips on each of the one or more struts to assist the user to hold and manoeuvre the device by the one or more struts alone.

The image capturing device is preferably able be operated in any of the following modes for focusing on the patient: Auto Focus (Single); Auto Focus (Continuous); and/or Manual Focus. The settings may be customised to apply to different applications of the medical device, such as when the device is functioning as an otoscope, fundoscope, ophthalmoscope or dermatoscope. These settings are preferably able to be automatically activated by putting on the individual adaptors for the otoscope, fundosccope, etc., described elsewhere in this patent specification.

The Manual Focus mode may provide a practitioner manual control over the contrast detection focus, phase detection focus or laser detection focus. The manual control is preferably exercised by controlling one or more of the following: ISO; shutter speed and/or; white balance.

The image capturing device is preferably able to capture a macro-scale image of the patient. The image capturing is preferably able to capture a micro-scale image (i.e. an optically and/or digitally enlarged or zoomed image) of the patient. The image capturing device may include a plurality of cameras which co-operate so as to provide improved imaging of a patient. Preferably, the plurality of cameras provide a monochrome mode to improves the dynamic range of regular shots by combining the data from standard RGB and light-sensitive black and white sensors. Preferably, the plurality of cameras include hybrid zoom technology which combines data from multiple cameras to produce higher resolution images for a better quality zoom. Preferably, a high-quality depth of field effect is also provided through both software emulation and the use of multiple focal lengths in the plurality of cameras.

In a preferred configuration, there is provided a plurality of image capturing device(s) located in the peripheral portion of the base (or in bulging portions bulging therefrom), and the image capturing devices may be moved with respect to the base and otherwise controlled to enable the image capturing device to capture a part of the patient directly viewable through the one or more openings of the base.

The base is preferably able to lockingly engage with an adaptor. Preferably, the base is able to lockingly engage with one or more adaptors so the device may be used as one or more of the following: an otoscope; an ophthalmoscope; a fundosccope; and/or a dermascope. The device may also be able to lockingly engage with other scope adaptor for use in other applications such as an endoscopy, laryngoscopy or colonoscopy.

The adaptor may have a complementary shaped portion to a portion of the base to provide a form fitting between the base and the adaptor. The base may include a protruding segment, and the adaptor may include a peripheral rim which can lockingly engage with the protruding segment. The locking engagement may be made with a locking pin which is able to be inserted through the adaptor into the base. The adaptor and the base may lock together magnetically, or via other means generally known to the skilled person in the art.

The device is preferably usable as a dermascope. The device may be connected to dermascope adaptor. The dermascope adaptor preferably includes a flat transparent plate. The flat transparent plate may include, or comprise, a magnifying lens. The flat transparent plate preferably includes a scale by which the medical practitioner can measure the size of features on the skin of the patient, when the flat transparent plat is placed on the patient's skin.

The device is preferably usable as an otoscope. The device may be connected to an otoscope adaptor, or otherwise engage with an otoscope adaptor. In one preferred form of the invention, an open otoscope adaptor allows performance of an operation or procedure through the otoscope adaptor. The open otoscope adaptor may include one or more apertures in the body of the adaptor. The otoscope adaptor may alternatively be closed. The closed adaptor has no apertures (e.g. holes or slots) in the body of the adaptor. The otoscope adaptor preferably includes a funnel shaped projecting portion.

The otoscope adaptor may be adapted for use with reusable and/or disposable specula or speculum sheaths. The reusable speculum sheaths or specula are preferably adapted to be sterilised. The reusable speculum sheaths or specula may be primarily made out of metal so as to be suited for sterilisation.

In a preferred form, the otoscope adaptor includes a tapered or domed lower portion. Alternatively, the lower portion may be substantially flat. Preferably, a projecting portion is located in the central axis of the lower portion of the otoscope adaptor (when viewed in plan view from directly above), the projecting portion including at least one aperture. Preferably, the projecting portion narrows as it extends outwardly from the lower portion. Preferably the projecting portion is frusto-conical in shape. Alternatively, the projecting portion may be shaped in a tubular form having substantially parallel sides. Preferably, the aperture of the projecting portion extends from an upper part of the projecting portion to a lower part of the projecting portion. The aperture in the projecting portion may extend into and form a continuous aperture with one of the at least one aperture in the lower portion of the adaptor.

In a particularly preferred form of the otoscope adaptor includes a plurality of apertures, the apertures being defined by a plurality adaptor struts which extend from a peripheral portion of the adaptor to the projecting portion of the adaptor. The plurality of struts provide structural support to the adaptor so that pressure may be applied to the projecting portion without damaging the form of the adaptor. Preferably, the plurality of struts enable gripping of the medical device by a person (ie. the medical practitioner). Alternatively, just one adaptor strut may be used.

Preferably, one or more of the one or more adaptor struts are orientable so that they align with one or more of the one or more struts of the base device. Preferably, one or more of the adaptor struts are approximately the same width as (or narrower than) one or more of the base device struts (when both the adaptor and base device are viewed in plan view from directly above).

Preferably, one or more apertures in the otoscope adaptor are orientable so that they align with one or more openings in the base device. Preferably, one or more of the apertures of the otoscope adaptor span approximately the same area as one or more of the openings in the base device (when both the adaptor and base device are viewed in plan view from directly above).

A speculum sheath may be mounted to the otoscope adaptor. In a preferred form, the projecting portion of the adaptor includes mounting means to mount a speculum sheath. Preferably, the mounting means includes a form fitting arrangement such that the adaptor includes a mounting element having a complementary shape to a mounting element on the speculum sheath. In a particularly preferred form, the mounting element on the adaptor is a furrowed strip extending around an external part of the projecting portion. Preferably, the complementary shaped mounting element on the speculum sheath is a protruding strip which extending around an internal part of sheath, such that the speculum sheath may be mounted by twisting the sheath on the projecting portion such that the two complementary mounting elements become engaged.

In a preferred form, the mounting element on the adaptor is adapted to engage with disposable speculum sheaths that are generally used in otoscopy (e.g. the disposable ear speculum provided by Welch Allyn).

In a preferred form, the otoscope adaptor may be adapted to include a speculum receiving portion. Preferably the speculum receiving portion is able to receive the speculum by sliding a lower portion of the speculum into the speculum receiving portion. In a particularly preferred form, the adaptor is adapted for receiving a reusable speculum. Preferably, the otoscope adaptor for slidably receiving a speculum is domed in shape. The speculum receiving portion may be located towards an upper part of the adaptor. The adaptor preferably includes a locking means to lock the speculum sheath in place. The otoscope adaptor preferably includes one or more cut-out sections, the upper part of which provides access to the speculum receiving portion. Preferably, there is one cut-out section comprising a section extending from an upper portion of the adaptor to a lower portion of the adaptor. Preferably, the cut-out section provides the medical practitioner access to the patient, and permits procedures such as those involving suction or removal or debris to be performed by inserting the suction tube or debris removing tool through the cut-out section in the adaptor.

Reusable specula may be shaped to include a rounded lip at the bottom, and the receiving portion of the otoscope adaptor may have a complementary shape so that the specula has a close fitting with the receiving portion. It is preferable for the medical device of the invention to be able to accommodate reusable specula, as some nose and throat specialist prefer the shape and/or design of existing reusable specula. Reusable specula may also be preferred by some medical practitioners as they are adapted to be sterilised (e.g. where they are made out of stainless steel).

Preferably, the adaptor for slidably receiving a speculum, or the adaptor onto which a speculum sheath is mountable, includes a securing means to secure the speculum or speculum sheath in place. In a preferred form, the securing means includes a slidable tab which slides into a securing arrangement in the adaptor. Preferably, once the speculum sheath or specula is received into or mounted on the adaptor, and the securing means is slid into the securing arrangement, the speculum or speculum sheath is secured together with the adaptor.

The adaptor and/or speculum sheath and/or specula is also preferably adapted to permit the medical practitioner to perform other operations via the aperture(s) and/or cut out(s) in said componentry, said aperture(s) or cut-out(s) being used separately or in conjunction with the opening(s) in the medical device. In particular, operations involving suction or removal or debris may be performed by inserting the suction tube or debris removing tool through an aperture or cut-out in the adaptor, the speculum and/or the speculum sheath, where the aperture or cut-out is located so as to limit the visual obstruction that the tube or tool provides to the medical practitioner during direct inspection of and operation on the patient.

The device may be operable with both a closed speculum sheath/adaptors/specula (i.e. without any aperture(s) or cut-out(s)) as well as an open speculum sheath/adaptor/specula (i.e. having a least one aperture or cut-out).

Preferably, the lower portion of one or more of the adaptors is adapted to lockingly engage with the base device.

Preferably the adaptor and/or speculum sheath includes light transmission means to transmit light from the at least one light source along a length of the adaptor for illumination of the patient. Preferably, the light transmission means includes fibre optics or an optical pipeline or other measures known to the skilled addressee. Preferably, the light transmission means is adapted to transmit light from a lower portion of the adaptor to an upper portion of the adaptor and/or an upper portion of the speculum sheath. In a particularly preferred form, the light transmission means is adapted to optically connect with the at least one light source to transmit the light therefrom to the upper portion of the adaptor and/or speculum sheath. Preferably, light transmission means are for illumination of the patient.

Preferably there is provided connecting means in the lower portion of the adaptor to connect the at least one light source to the light transmission means in the adaptor.

The at least one light source may be connected to fibre optics in the adaptor and/or speculum sheath to provide illumination of the patient at the distal end of the adaptor and/or speculum sheath.

The device is preferably able to be used as a combination of two or more of the following: an oroscope, an ophthalmoscope, a dermatoscope, an otoscope, fundosccope. The device the subject of the invention is preferably also able to be used with other diagnostic tools or device, including a slit lamp or other slit beam tool, or an ear microscope, for example.

The device is preferably usable as an oroscope or as an ophthalmoscope without requiring an adaptor. The device, when used as an ophthalmoscope, may be used in conjunction with an externally provided slit beam to assist in the investigation of the lens or cornea. The externally provided slit beam may derive from a portable slit beam emitting tool such as a handheld tool. The slit beam tool may be in in the form of a pen whereby a light source within the pen is turned on or offer by pushing a button. The slit beam tool may include an adjustable slit beam width and/or slit beam length, for example by twisting one segment of the pen relative to another and/or otherwise moving part of the handheld tool relative to another part of the tool and/or via a scroll wheel or like adjustment means. The intensity of the slit beam light source may be raised or lowered. The intensity of the light source may be controlled by buttons or other controlling means located on the handheld slit beam tool itself. In a preferred form, the handheld slit beam tool is able to interact with controlling means located on the medical device (and more particularly, controlling means located on the base of the medical device). Preferably, the interaction is by way of wireless communication by Bluetooth or Wi-Fi or the like between the slit beam tool and the device.

The device may also be adapted for connection to a fundosccope adaptor. Preferably, the fundosccope adaptor includes a fundus lens that, when the adaptor is connected to the base of the device, aligns with at least one image capturing device on the base of the device. Preferably, when the adaptor is connected to the base of the device, the fundus lens is aligned with at least one of the light sources on the base of the device. Preferably, the fundosccope adaptor includes light transmission means along a length of the adaptor. Preferably, the light emitted by at least one light source on the base of the device is able to be transmitted by the light transmission means from a first side of the adaptor to a second side of the adaptor. Preferably, the transmitted light is able to be directed to a central axis which is aligned with the central axis of the fundus lens. Preferably, the image capturing device is able to automatically-focus the image of the fundus provided by the lens so that the captured image is a focussed image of the fundus of a patient. Preferably the automatic focussing is performed by the image capturing device (together with the software controlling same) detecting distance between the eye of the patient. Preferably the automatic focussing is performed by the image capturing device (together with the software controlling same) detecting the alignment of the camera with the central part of the eye. The device and adaptor are preferably shaped so that the outer surface of the device and fundosccope adaptor are together manoeuvrable for examination of the fundus without contacting the patient (e.g. the patient's nose). The adaptor may be frustoconical in shape.

Preferably, the fundosccope adaptor is for use with non-polarised, polarised and green light provided by the at least one light source on the base of the device.

Alternatively, the base of medical device may include the fundus focussing, as described above.

In one preferred embodiment of the invention, the image capturing device for alignment with the fundus lens may be located on the peripheral portion of the base so that the bulk of the medical device may be manoeuvred away from the nose or other protruding feature of the patient. In this embodiment the device may not provide for direct inspection of the eye of the patient (though it will at least provide for direct inspection of the region around the eye) as the eye may be obscured by the peripheral portion of the base device. In such an embodiment, the display will provide for indirect inspection of patient.

It will be appreciated by the person skilled in the art that for certain medical inspections, procedures or operations it may be preferable for the device to be use for indirect inspection of the patient only. This may be where, for example, the comfort of the patient is compromised by the close proximity that the medical practitioner needs to have to the patient to perform direct inspection.

It will also be appreciated by the person skilled in the art that for certain medical inspections and/or operations it may be preferable for the device or adaptor or other components connecting to the device to be shaped to provide for better manoeuvrability of the base of the device, adaptor or other connector vis-à-vis the patient. In particular, it may be preferable for direct inspection of or access to the patient to be conducted using a combination of the space within and outside the outer perimeter of the base of the device, adaptor or other connector (i.e. not solely via the openings or apertures within the base, adaptor or other connector).

The invention extends to a method of using the medical device and an externally provided slit beam, wherein the externally provided slit beam is able to be positioned relative to the medical device such that the medical device is located proximate to the patient, and the externally provided slit beam is located laterally thereto, and the light from the slit beam hits the patient at such an angle that the medical practitioner is able to obtain slit beam assisted inspection of the patient via the medical device.

The medical device may be connectable to a handle. The handle may be connectable to the peripheral body. The handle may be screwed into the peripheral body, lockably slide into the body or otherwise securely engage with the body by means known to a person skilled in the art.

The medical device may be also connectable to a frame, on one part of which the patient is able to rest his or her head in a stable manner for inspection in a method similar the method by which the slit lamp is customarily used. To the same frame the display of the medical device, the base and/or the display and/or an externally provided slit beam may be attached. In this way the medical practitioner may locate the base and the display so that they can inspect the patient hand keep both hands free for performing an examination, procedure or operation. The frame may be desk-mountable, wall-mountable, otherwise-mountable to regular objects found in a medical practitioner's suite. Alternatively, the frame may be freestanding.

Another embodiment of the invention which permits the medical practitioner to inspect the patient but keep two hands free includes a wearable accessory which is wearable by the patient or medical practitioner, and to which the medical device is movably attached. Preferably the wearable accessory comprises a wearable head accessary such as a headband or other headwear, or another accessory wearable on another body part such as the shoulder or arm of the patient or medical practitioner.

One or more arms may extend from the wearable accessory and/or the frame, the one or more arm(s) preferably including one or more or more joints or other movable elements to enable the base of the device (which is attachable to the one or more arm(s)) to be positioned in the appropriate location and to permit the medical practitioner to use two hands to conduct an examination of, or perform an operation or procedure on, the patient. Preferably, the one or more arms(s) are telescopic.

Preferably, the one or more joints include ball joints to permit multi-directional movement of segments which are connected by the ball joints.

The base may be attachable to the one or more arm(s) via a ring into which the device is able to slidably engage, or otherwise securely attachable to permit use of the device for inspection, procedural or operational purposes as described above. The base may be attachable to the one or more arm(s) via a movable joint, and in particular a movable ball joint is preferred. The one or more arm(s) may also be attached to the wearable accessory or frame via a movable joint, and in particular a movable ball joint is preferred.

Preferably, the wearable accessory is adjustable so that it may fit a variety of body part shapes or sizes.

The wearable accessory and/or frame preferably is able to be used, together with the device, for eye and/or ear examinations, operations and/or procedures.

In a preferred form, the wearable accessory is a headband having a plurality of telescopic arms. Preferably, two of the telescopic arms are each adapted to attach to the base device and the headband, and one of the telescopic arms (the third arm) is adapted to attach to the base of the device and contact a part of the patient. Preferably, the third arm includes a soft end for softly contacting a part of the patient. Preferably, the third arm is adapted to contact the cheek or surrounding region of the patient. Preferably, the arms operate as a tripod to hold the medical device in position relative to the patient.

The invention may comprise a kit of parts including the frame, the arm and the device.

The invention may comprise kit of parts including the wearable accessory, the arm and the device.

The device and/or an adaptor for use therewith is preferably waterproof.

The device may include a rechargeable battery located within the device. The device preferably includes charging points on the outer surface of the device so that the device can be charged.

The base of the device may be openable to permit replacement of a battery, a light element or to perform repairs.

The device may include a wired or wireless connection which provides the ability to charge the battery of the device, for example via a mini-USB port and cable or an inductive power receiver applying the Qi wireless standard for use with a charging pad. In some applications, the wired or wireless connection for charging may also be used as the means for connecting the image capturing device to a display.

The device may be provided in the form of a kit including the base device and one or more of the adaptors or speculum sheaths described herein. The kit or the device alone may be provided in a travel bag to provide ease of transportation.

According to a further aspect of the invention, there is provided a medical device for inspecting a patient, the device including:

a base;

an image capturing device for capturing images of the patient; and means to communicate the captured image to a display for displaying said captured images;

wherein the base includes one or more openings through which the patient is able to be directly accessed, the one or more openings being located around the image capturing device.

Preferably, the display is located on a surface of the medical device such that the patient is able to be inspected via the display, and the patient able to be directly accessed, at the same time (i.e. contemporaneously).

The features described in relation to one or more aspects of the invention are to be understood as applicable to other aspects of the invention.

Other aspects of the invention are also disclosed.

Advantageous Effects of Invention

Many advantages are achieved by the present invention, many of which will be well appreciated by a skilled person—and some of which are outlined below. The use of the medical device can provide uses with different attachments for varying optical inspections and treatments. The invention lends itself especially well to low cost but more effective use of direct and indirect inspection, and access to the patient for procedures or operations.

Benefits of the invention to be described in more detail, include one or more of:

a. Easy to use b. Easy to handle c. Cost effective, as multiple types of inspections with one device d. Preserves visual-motor coordination during inspection as medical practitioner's direct view of and access to the patient is not obstructed e. Permits a combination of direct visual inspection and enhanced digital image inspection, contemporaneously (and in particular, during the setting of one examination, procedure or operation)

f. Preserves ability to perform operations (when used as an otoscope)

BRIEF DESCRIPTION OF DRAWINGS

Notwithstanding any other forms which may fall within the scope of the present invention, preferred embodiments of the invention will now be described, by way of example only, with reference to the accompanying drawings in which:

FIG. 2A is a side perspective view of a schematic drawing of the medical device according to a second preferred embodiment of the present invention, including a base designed to lockingly engage with an adaptor;

FIG. 2B is a bottom perspective view of a schematic drawing of the medical device in FIG. 2A;

FIG. 2C is an elevated side perspective view of the image capturing device and dual struts extending therefrom, of the medical device in FIG. 2A;

FIGS. 6A and 6B depict an example embodiment of a schematic representation of an externally provided slit beam comprising a slit beam pen, from a side perspective and front perspective view.

FIG. 7A depicts an example embodiment of a schematic representation of a wearable accessory and a medical device connected thereto by three arms, from a side perspective view.

FIG. 16A is a front perspective view of the medical device depicted in FIG. 9 and a schematic drawing of second preferred embodiment of an otoscope adaptor (open) and of a disposable speculum sheath.

FIG. 16B is a rear perspective view of the otoscope adaptor depicted in FIG. 16A.

FIG. 17 is a front perspective view of the medical device depicted in FIG. 9 lockingly engaged with the otoscope adaptor and disposable speculum sheath depicted in FIG. 16, in use.

DESCRIPTION OF EMBODIMENTS

A medical device is described and depicted herein in connection with illustrative but non-limiting preferred embodiments with reference to the drawings.

The structure, principle and operation of the described medical device, will be described as will be appreciated by those skilled in the art.

Structure

FIGS. 1 to 5 depict medical devices for inspecting a patient and adaptors suitable to be used therewith in accordance with preferred embodiments of the invention.

Figures 1A, 1B, 1C:
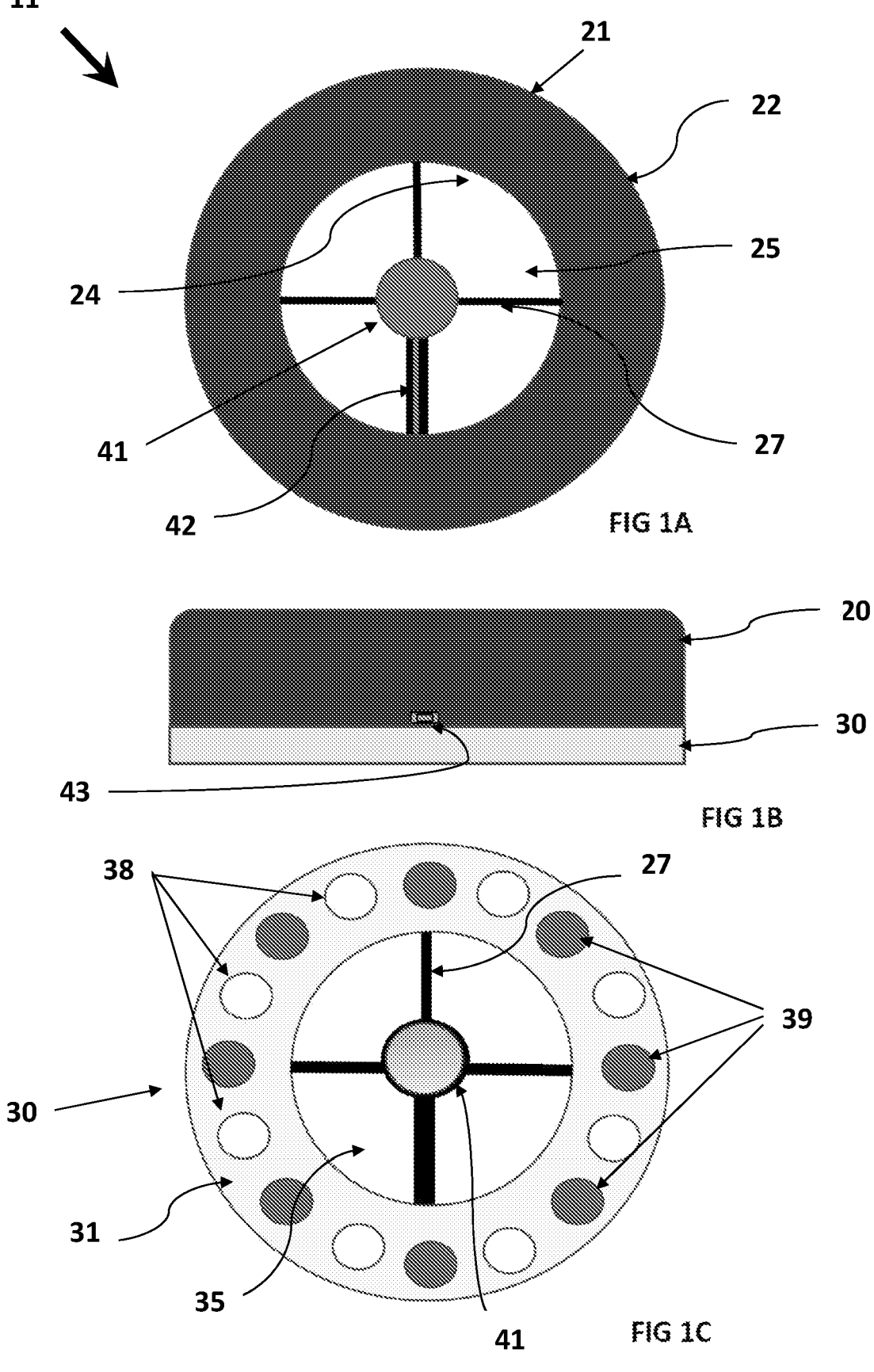
FIG. 1A is a top perspective view of a schematic drawing of the medical device according to a first preferred embodiment of the present invention.
FIG. 1B is a side perspective view of a schematic drawing of the medical device in FIG. 1A.
FIG. 1C is a bottom perspective view of a schematic drawing of the medical device in FIG. 1A.

FIGS. 1A to 1C depict a first preferred embodiment of the medical device 11 which is the subject of the invention. In this embodiment device, the display (not shown) is not located on the medical device itself. The base 20 has a peripheral portion 21 in the form of a ring and an inner open area 25. The peripheral portion 21 in the form of a ring has an inner ring 22 and an outer ring 24 such that the ring is an annular shape in which both the inner ring and outer ring are concentric circles. However, in other embodiments, instead of a circular inner ring the peripheral portion of the base 20 can have an inner hexagon shape (or other shape, e.g. a polygon—not shown), and instead of an outer ring it may have an outer octagon shape (or other shape, e.g. a polygon—not shown). The inner open area 25 extends through the body from a top side to a bottom side so as to provide an open channel.

The medical device 11 includes an image capturing device 41 which in this form comprises a camera including a lens. The camera 41 is mounted within the peripheral portion and is surrounded by the inner open area 25, and centrally located within the peripheral portion by four struts 27 extending from the inner ring 24 to the camera 41. The four struts 27 are spaced and can form a cross shape or X-shape. However, there can be in other forms a different number of struts such as one, two or three.

The image capturing device 41 in other forms can include CMOS, sCMOS or CCD digital sensor.

The image capturing device 41 has controls (not shown) for altering usage such as focus, ISO, shutter speed. It can also provide controllable zooming. There could be one or a selection of operational modes such as auto focus, continuous auto focus or manual focus.

The image that the image capturing device 41 captures can be actively manipulated at the time of capture or digitally manipulated at or after capturing. For example, the zooming can be digital zooming or lens manipulation at time of capture can provide optical zooming. The images captured by the image capturing device are still frames or video footage. The image capturing device 41 is able to take image snapshots during the course of capturing a digital video recording.

One of those struts 27 can include at least part of a means to communicate the captured images to a display for displaying captured images. This can be wire connection 42 along one of the struts 27 to an outlet connector 43 in the outer peripheral portion 21.

The outlet connector 43 can connect to a display (not shown) by wired connection or wireless connection by Bluetooth or Wi-Fi or the like. Such elements can be within the peripheral portion 21 with the outlet connector 43 being a physical connector for wired connection or an emitting connector for wireless connection.

The display can be locatable proximate to the base 20 so that the practitioner can undertake direct inspection of the patient or access the patient through the open area 25, 35 or undertake indirect inspection by the images captured by the image capturing device 41 and sent to the display for displaying the captured images. This display can be free standing and locatable proximate to an opening of the base 20. However, in a preferred form the display is attachable to a person via an attachment clip or attachable to a wrist of the person. In this way the practitioner can be controlling the medical device with one hand and can move the other hand to a viewing position where required without having to move the controlling hand and with minimal movement of the head. Therefore, the operation by the practitioner remains focussed and does not alter the examination set-up.

An important element is that the inner open area 25 remains a relatively open channel to allow direct optic viewing and access therethrough by the practitioner. It also requires other elements of the medical device 11 to be within the peripheral portion 21 or to be aligned with the peripheral portion so as not to hinder the direct viewing and access and to provide the direct viewing as close as possible to the view by the image capturing device 41.

In one form the inner ring 24 of the medical device is about 30 millimetres while the outer ring 22 of the peripheral body 21 is about 55 to 65 millimetres in diameter. However, the camera 41 can be of the order of 5 to 10 millimetres. This means the camera 41 only takes up a very small percentage of the inner area 25 allowing a relatively large open area 25 ready direct open channel for viewing or access therethrough. Alternatively, the diameter of the inner ring 24 may be larger, such as about 60-65 millimetres and the diameter of the outer ring may be about 80-90 millimetres, so that the ring is much thinner, and the device provides an even greater proportion of open area for viewing or access.

One of those elements of the medical device 11 to be within the peripheral portion 21 or to be aligned with the peripheral portion so as not to hinder the direct viewing or access is for the holding of the device to be spaced from the camera 41 and in effect be the outer ring 22 of the peripheral portion 21. In this way the fingers of the practitioner are not around the camera 41 and providing obstruction for direct view or access by the practitioner but instead are spaced from the camera 41 with the open area 25 providing the direct channel for direct viewing or access alongside the camera 41.

Another of those elements of the medical device 11 to be within the peripheral portion 21 or to be aligned with the peripheral portion so as not to hinder the direct viewing or access is for the medical device 11 of this embodiment to have a light source housing 30 with a ring of light sources 38, 39 for illuminating the patient for inspection. The light sources 38, 39 are located on a lower surface of the base 20 in a connectable or integral annular ring shaped light source housing 30 having peripheral portion 31 which corresponds with and aligns with the annular ring shape of the peripheral portion 21 of the base 20. The ring shape of the light source housing 30 has a central open area 35 that aligns with the open area 25 of the base and thereby continues the open channel through the entire medical device 11. A further substantial advantage of the light source 38, 39 being in the peripheral portion 31 is that it is outside both the central open areas 25, 35 and outside the camera 41. Therefore, the illumination that the practitioner sees with direct inspection through the open channel formed by the open areas 25, 35 is the same illumination seen by the camera 41. Even further it can be seen that light reflection and viewing angle are as close as possible as being the same between the direct viewing through the open channel formed by the open areas 25, 35 to the same light reflection and viewing angle seen by the camera 41.

The light sources comprise a combination of blue and white light sources 38, 39 such as blue and white high intensity light emitting diodes (LEDs). The light sources are controllable in collective intensity as well as separate operation of the of blue and white light sources 38, 39 to provide a range of lighting.

Another of those elements of the medical device 11 located so as not to hinder the direct viewing or access is for the controls of the lighting (not shown) to be on the outer surface of the peripheral portion 21. Still further the controls (not shown) of the image capturing device 41, such as a camera and a lens, are located on the outer surface and preferably the upper outer surface of the peripheral portion 21 so that they are directly accessible by the practitioner without changing viewing angle through the medical device 11.

FIGS. 2A to 2C depict a second preferred embodiment of the medical device 11 which is the subject of the invention. In this form there are substantial similarities to the first embodiment. However, the medical device 111 includes a base 120 with a connected lighting element 130 having a peripheral portion 131 that is shaped to be attachable to further attachments. This is achieved by the outer ring 132 of the light source housing 130 of the medical device 111 having a frictional connecting ridged surface that can interfit with the further medical attachment.

Another difference of this embodiment is that there are only two struts 127 holding the image capturing device 41 such as a camera in the centre of the open area 125 formed by the annular configuration of the ring of the peripheral portion. A particular benefit of the only two struts is increased unobstructed area for viewing or accessing therethrough. However, it also allows the struts 127 and/or the inner ring 122 of the peripheral portion 131 to be used wherein the device is able to be handled by the thumb and one or more finger by a person for inspecting the patient. Alternatively, the medical device is still able to be handled by the peripheral portion 21.

Figure 3A:
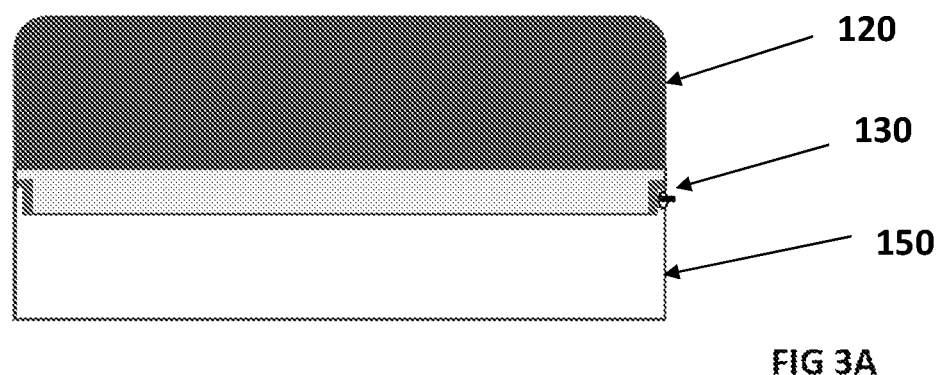
FIG. 3A is a side perspective view of a schematic drawing of the medical device according to a preferred embodiment of the present invention, including a dermatoscope adaptor.
Figure 3B:
FIG. 3B is a side perspective view of the dermatoscope adapter in FIG. 3A.
Figure 3C:
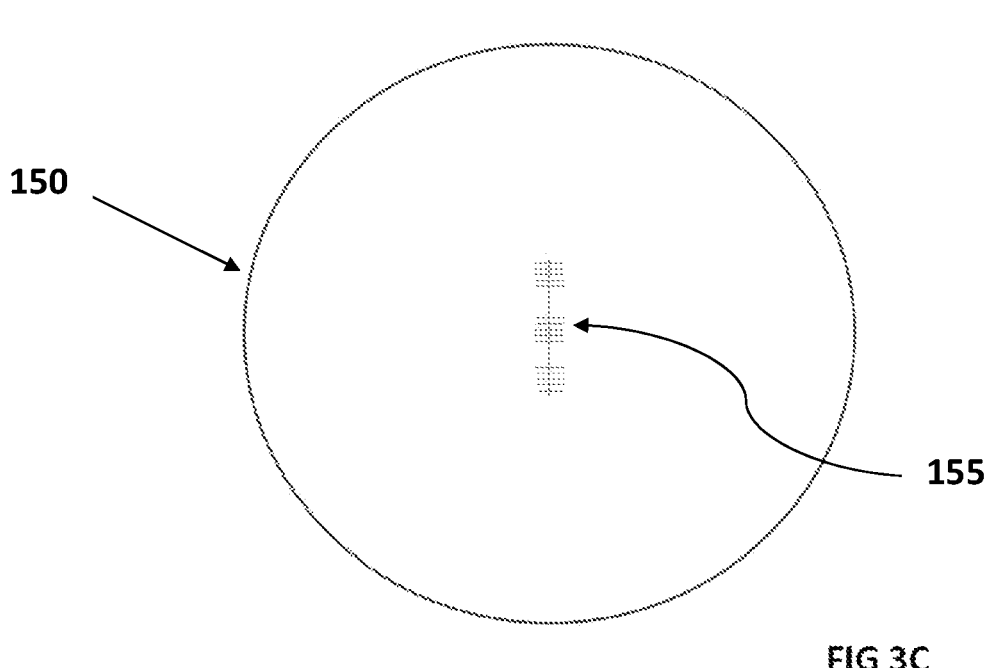
FIG. 3C is a bottom perspective view of the dermatao-scope adapter in FIG. 3A.

FIGS. 3A to 3C depict a preferred embodiment of the medical device 11 which is the subject of the invention including a dermatoscope adaptor 150. As shown the base 120 with the connected lighting element 130 is able to lockingly engage with an adaptor 150. The adaptor 150 has a peripheral rim 153 with recess therebetween sized and shaped to be a complementary shape to the light source housing 130 having a protrusion with reduced diameter so as to provide a form fitting between the light source housing 130 and the adaptor 150. This is achieved in this form by the base including a protruding segment, and the adaptor including a peripheral rim. The dermatoscope adaptor 150 includes a dermatological optical ruler 155.

The adaptor and base are able to lock together. This locking can be by internal frictional fit or magnetically or by screw means. It can be seen that this allows for different adaptors to be connected to the main body 120 which has integral or connected light source housing 130. These adaptors can be any one or more of an oroscope, an ophthalmoscope, a dermatoscope, and an otoscope. However, it could be connection to a different form or variety of one of these devices.

Figure 4A:
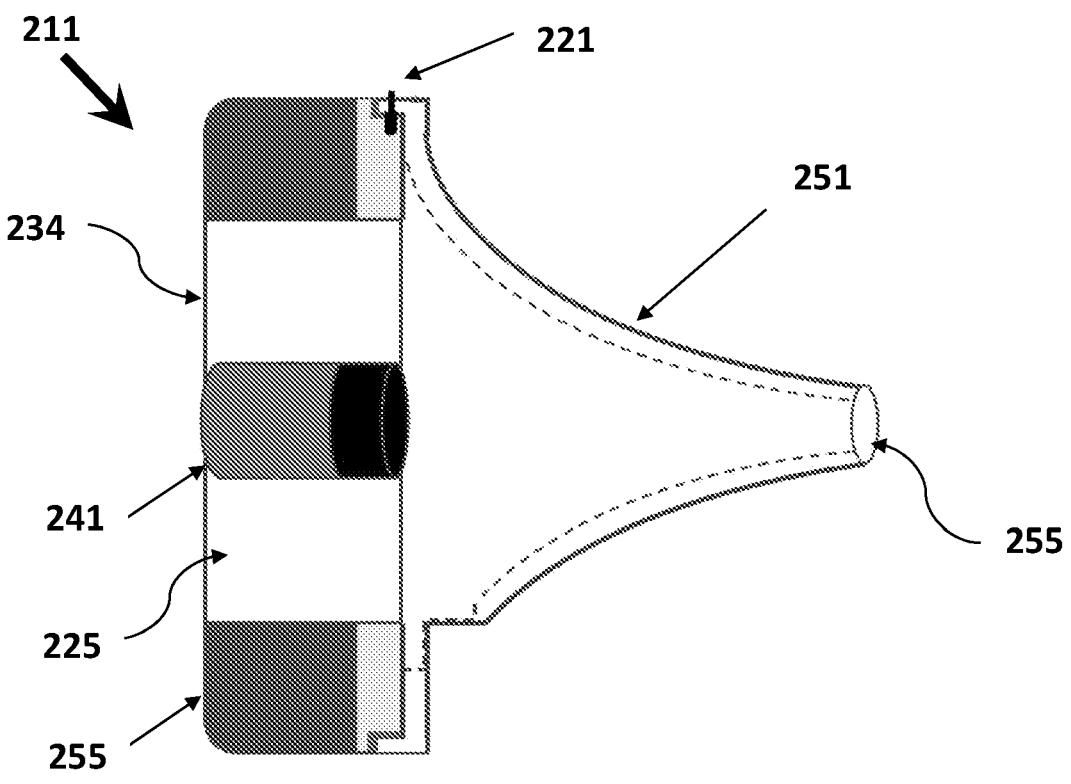
FIG. 4A is a side cross-section view of a schematic drawing of the medical device according to a preferred embodiment of the present invention, including an otoscope adaptor.
Figure 4B:
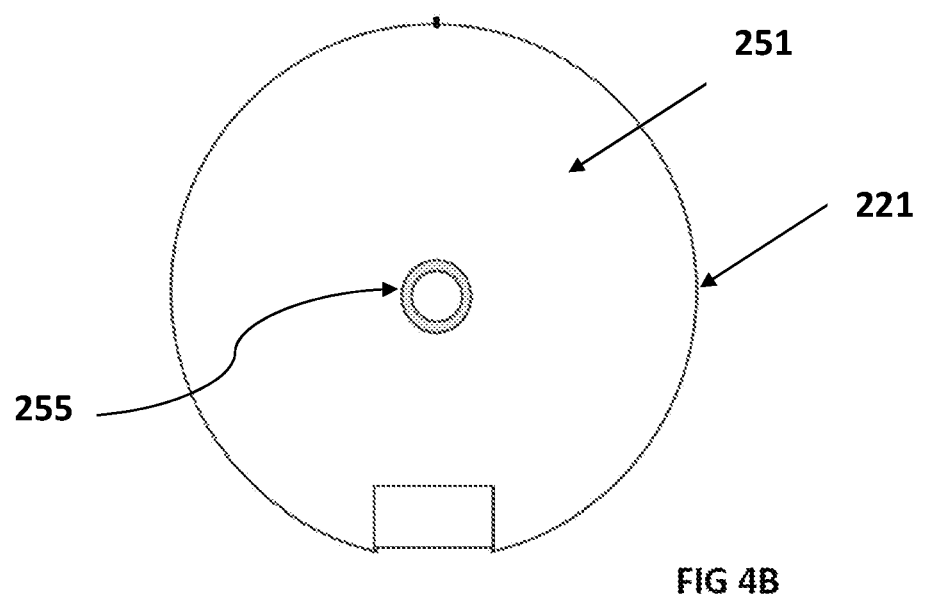
FIG. 4B is a front perspective view of the ophthalmoscope adapter in FIG. 4A.
Figure 5:
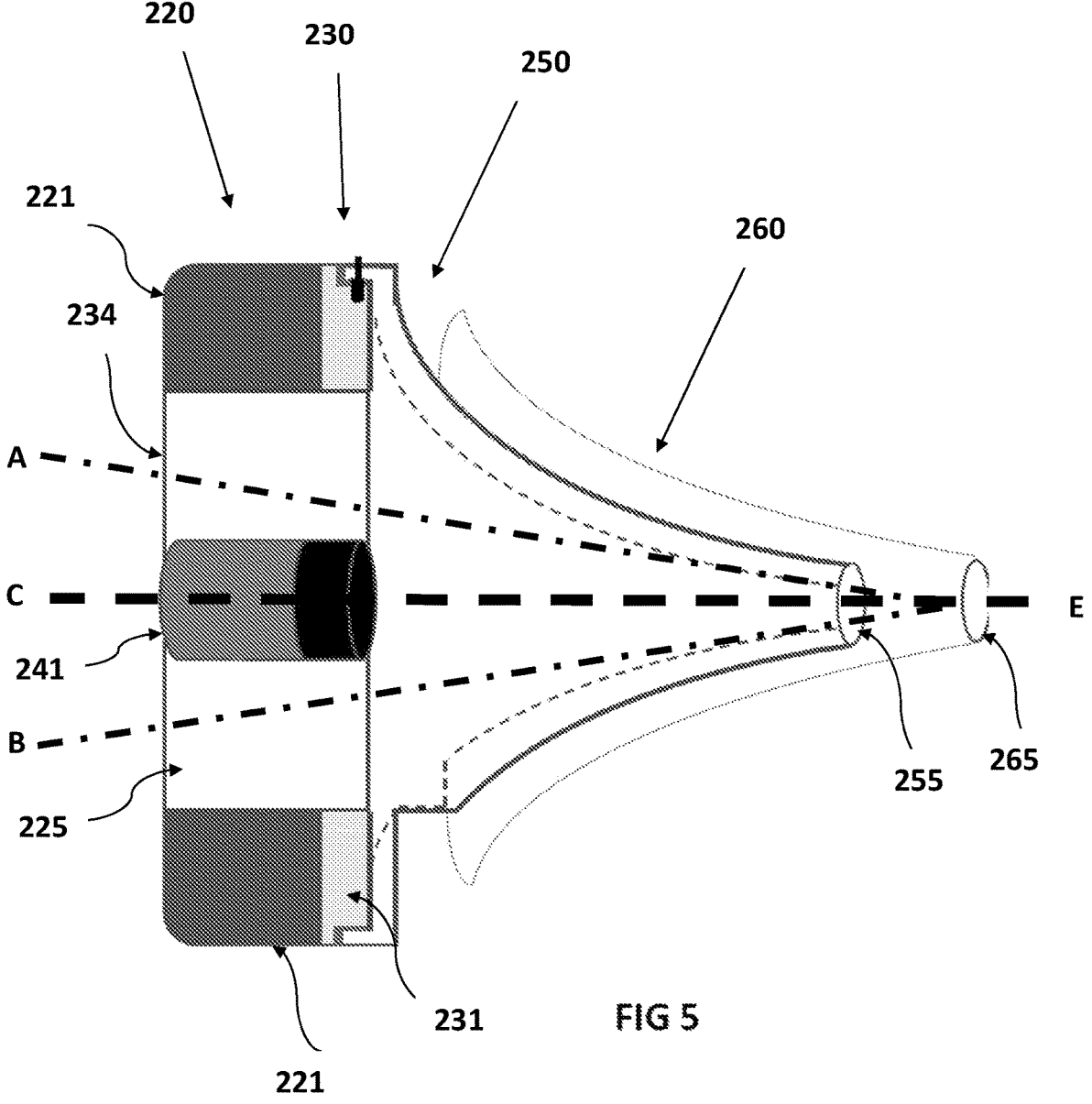
FIG. 5 is a side cross-section view of a schematic drawing of the medical device according to a preferred embodiment of the present invention, including an otoscope adaptor and a speculum sheath.
Figure 8:
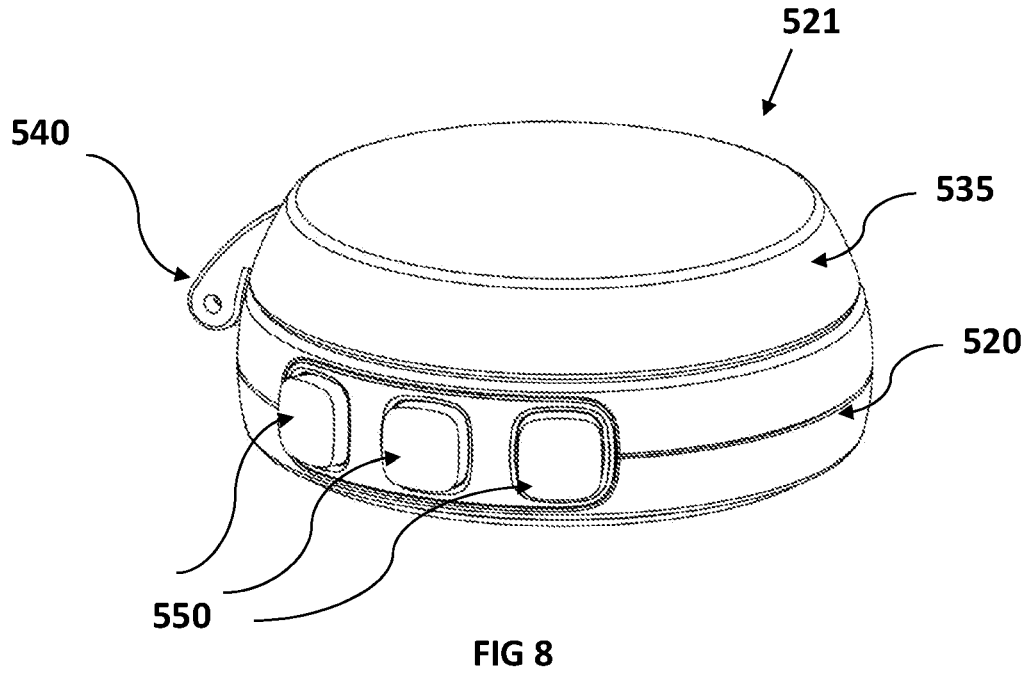
FIG. 8 is an elevated perspective view of a schematic drawing of the medical device according to a third preferred embodiment of the present invention.
Figure 9:
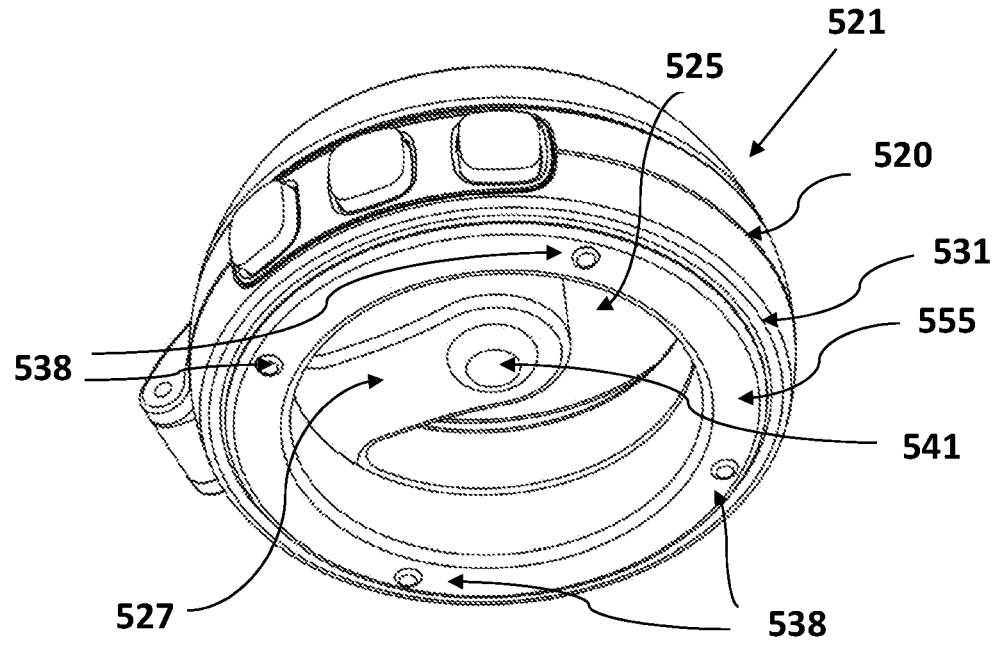
FIG. 9 is a bottom perspective view of the medical device depicted in FIG. 9.

Referring to FIGS. 4A to 4B and 5 there is depicted a preferred embodiment of the medical device 211 which is the subject of the invention including an otoscope adaptor 250 and further in FIG. 5 with a speculum sheath 260 overlying the otoscope adaptor 250.

However, the basics of the medical device 211 are similar to the other embodiments 11 and 111 in that there is a base 220 which has a peripheral portion 221 in the form of a ring and an inner open area 225. The peripheral portion 221 is an annular shaped ring in which both the inner ring and outer ring are concentric circles. However, in other embodiments, the inner and outer rings can have different shapes. The medical device 211 includes an image capturing device 241 which in this form comprises a camera including a lens.

As shown the base 220 with the connected light source housing 230 is able to lockingly engage with an adaptor 250 in the form of an open ended funnel shaped outer wall 251 which has the larger opening with a peripheral rim with recess therebetween sized and shaped to be a complementary shape to the light source housing 230 having a protrusion with reduced diameter so as to provide a form fitting connection between the light source housing 230 and the adaptor 250. The other end of the otoscope adaptor 250 is an end opening 255 which is the viewing opening of the patient's ear.

It can be seen that the viewing direction of the camera 241 is along the axis of C-E. This is a direct line. However, the medical device 211 is also allowing the practitioner to undertake direct viewing through the open channel formed by the open area 225 created by the peripheral body retaining the camera at a spaced inner position. Therefore, the practitioner has viewing angles including B-E and A-E for direct inspection which are very close to the angle and illumination that is captured by the camera. Also, the initial positioning of the device is more readily achieved.

If required, the speculum sheath 260 overlying the otoscope adaptor 250 can be overlayed with its end opening 265 correlating with the end opening 255.

The light source housings of the preferred embodiments 30, 130, 230 of the medical device depicted in FIGS. 1B, 2A, 3A and 4A are each adapted to be removed from the base of each device 20, 120, 220 to enable access to batteries and other components located in each of the base devices. When the light source housing is connected to the base device, the combined structure is waterproof.

FIGS. 6A and 6B depict a slit beam providing pen 300. A light source is located within the pen 300 (light source not shown) which provides light out of the base of the pen 330. The pen includes a central segment 310 about which the about the section of the pen 330 to the right may be twisted relative to the section to the left of the central segment 310. The twisting of the right section causes the width of the slit 340 to increase and therefore a wider slit beam of light to emanate from the base of the pen 330. The length of the slit beam 355 is controlled by shutter means akin to a camera shutter which operates to narrow the length of the beam as the shutter is closed. The length of the slit beam 355 is adjusted by a scroll wheel located 350 on the pen. Depending on the direction that the scroll wheel 350 is rotated, the length of the beam 355 either increases or decreases. The light source is activated by pushing the pen button 320, and the intensity of the light source is able to be increased by further pushes of the pen button 320, or via use of a second scroll wheel (not shown) located on the pen 300.

FIG. 7 depicts a headband 450, which is connectable to a base device 440 via telescopic upper arms 460, and telescopic lower arm 470 with cushioning end 475. The headband includes a movable ball joints 410, each of which is attached to an arm 460 at one end, and a medical device holder 400 at the other end. The telescope arms 460, 470 include a releasable locking mechanism (not shown) to lock the length of the arms, and then release again. The headband 450 permits the device to be moved so that the patient can be clearly viewed or accessed by the medical practitioner using the device. The movable ball joints 410 permit the arms and the base device to be moved so that the base device 440 is close to or touching the patient as required by the medical practitioner. The cushioning end 475 is adapted to softly rest on the cheek of the patient. Once the base device is located, the medical practitioner can use both hands to conduct an investigation, procedure or operation, without needing to physically hold the device 440.

Although not depicted in the figures a frame may be provided for receiving a head of a patient, such that the patient's forehead is able to rest on an upper curved element of the frame and the patient's chin is able to rest on a lower curved element. An arrangement of arms similar to that described in relation to FIGS. 7A and 7B, and with generally the same functionality may be attached to such a frame.

Both the headband 450 and the frame (not shown) permit the base to be located relative to the patient in a fixed arrangement, such that the base does not move significantly relative to the area of the body which is being inspected or accessed. These arrangements permit the medical practitioner to conduct any operation or procedure which requires the use of two hands, and in particular eye or ear operations or procedures.

FIGS. 8 to 11 depict a third preferred embodiment of a medical device 521, the device including a base 520 and an image capturing device 541 located in the base. The medical device 521 includes wiring (not shown) to communicate images captured by the image capturing device 541 to a display 570 (see FIG. 10). The image capturing device 541 is embedded in the device and able to capture a macro-scale and micro-scale images of the patient by use of optical and/or digital zooming.

The base 520 includes an opening 525 which through which a patient may be directly inspected and/or accessed. The opening 525 is located around, and substantially surrounds, the image capturing device 541.

The device 521 includes a lid 535 which is pivotable with respect to the base 520 via hinge 540. When in the open position (see FIG. 10) the display 570 is adjacent to the opening 525, on the inner surface of the lid 535, and a patient is directly viewable and/or accessible through the opening 525 of the medical device. The medical device 521 provides for a first (direct) inspection of a patient (not shown) through the opening 525, and for a contemporaneous second (indirect) inspection of the patient by inspection of the images of the patient captured by the image capturing 541 device on the display 570.

The base 520 of the device includes a ring shaped peripheral portion 531. The opening 525 is located between the peripheral portion 531 and the image capturing device 541. The image capturing device 541 is located within peripheral portion 531, and within a first a plane defined by an upper surface 554 of the peripheral portion, and a second a plane defined by a lower surface 555 of the peripheral portion.

The base 520 of the device includes a single strut 527 extending inwardly towards a central axis of the device and from the peripheral portion 531 to locate the image capturing device 541 centrally within the peripheral portion 531.

The medical device depicted in FIGS. 8 to 11 includes four light sources 538 for illuminating a patient, the light sources being located on the lower surface 555 of the peripheral portion of the base 531. The device further includes controls in the form of buttons 550 located on the upper surface 554 of the base, as well as a side surface of the base. The buttons control the optical and digital zooming of the camera, and generally navigating around the menus and options provided by the software governing the image taking device and the images (e.g. for saving and/or communicating the images).

Figures 10, 11:
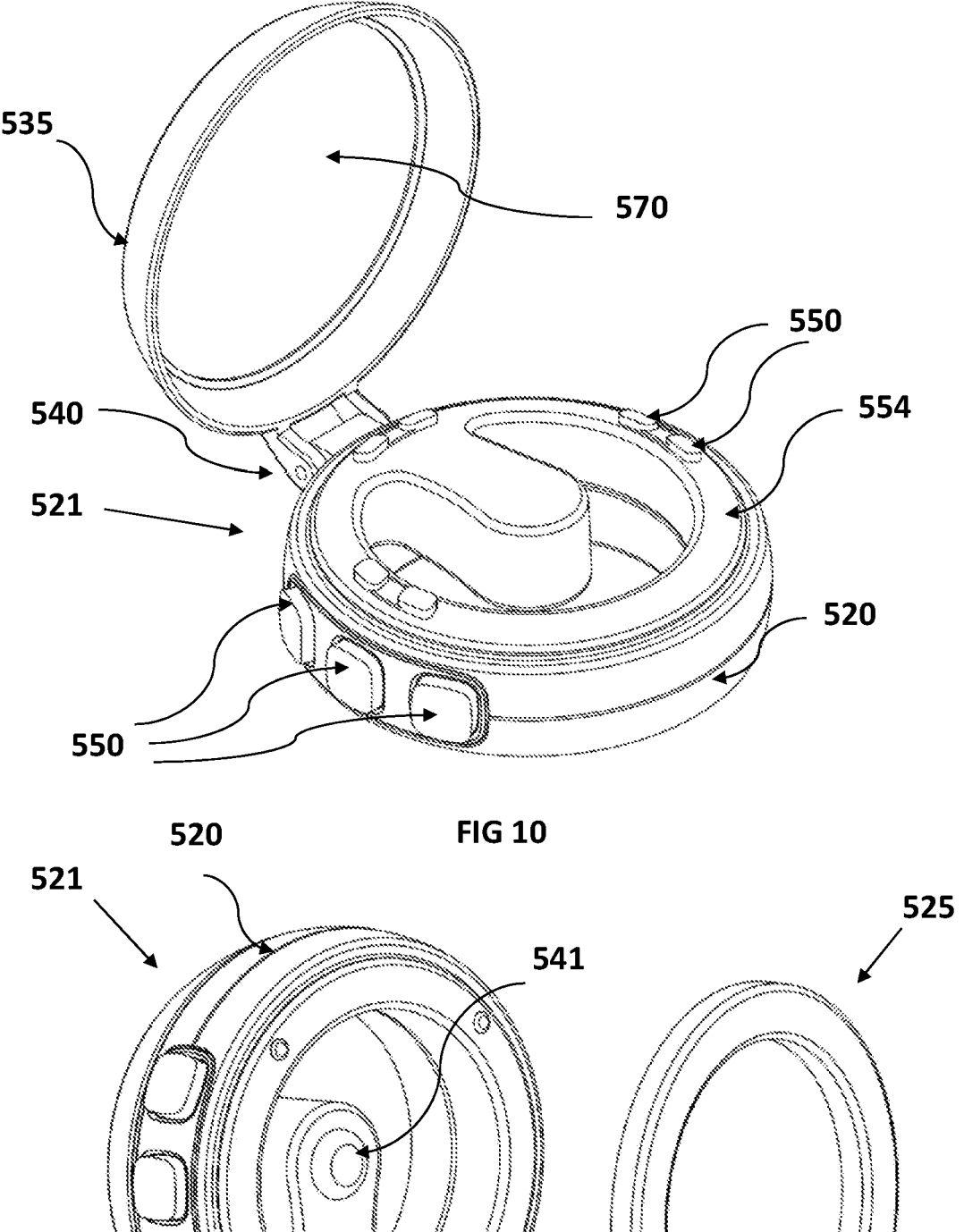
FIG. 10 is an elevated perspective view of the medical device depicted in FIG. 9, where the lid is in a raised position.
FIG. 11 is a front perspective view of the medical device depicted in FIG. 9 and separate cover.
Figures 14, 15:
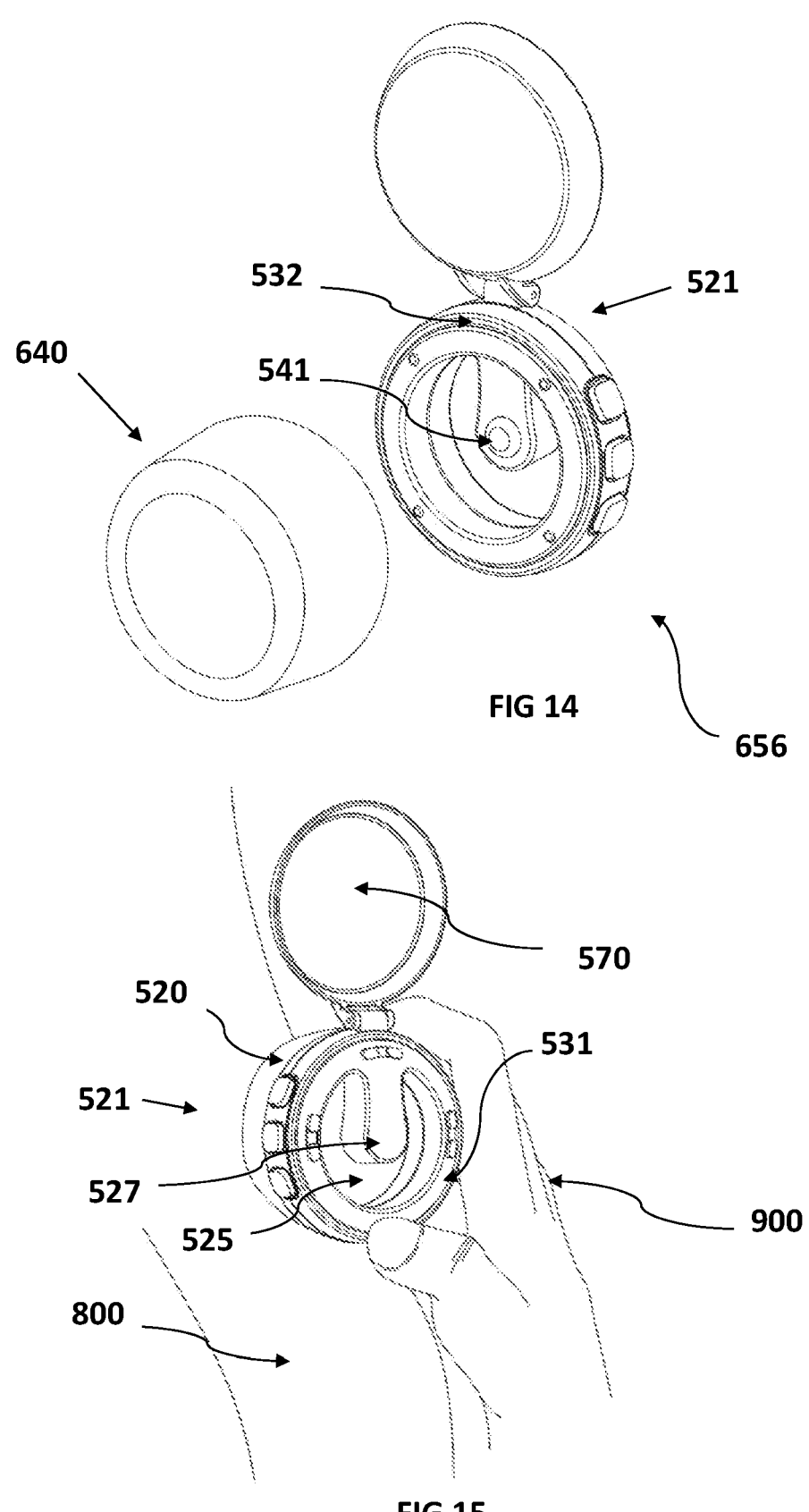
FIG. 14 is a front perspective view of the medical device depicted in FIG. 9 and a separate schematic drawing of second preferred embodiment of a dermatoscope adaptor.
FIG. 15 is a front perspective view of the medical device depicted in FIG. 9 engaged with the dermatoscope adaptor depicted in FIG. 14, in use.

As depicted in FIG. 11, the base 520 includes an outer ring 532 comprising a frictional connecting ridged surface that can interfit with a rounded glass cover 525 or other adaptors (see, for example, adaptors depicted in FIGS. 14, 16A/B and 19). The glass cover 525 is removable and therefore able to be hygienically cleaned separate from the base device.

Figure 12:
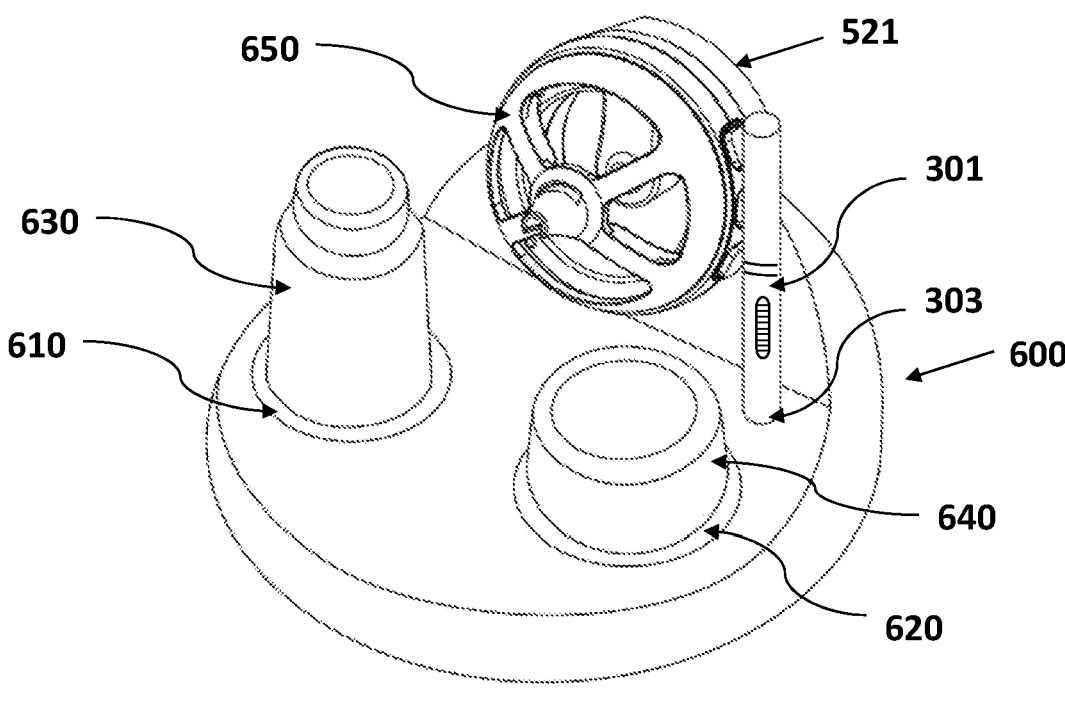
FIG. 12 is an elevated perspective view of the medical device depicted in FIG. 9 (including an adaptor) and a first wireless charger.
Figure 13:
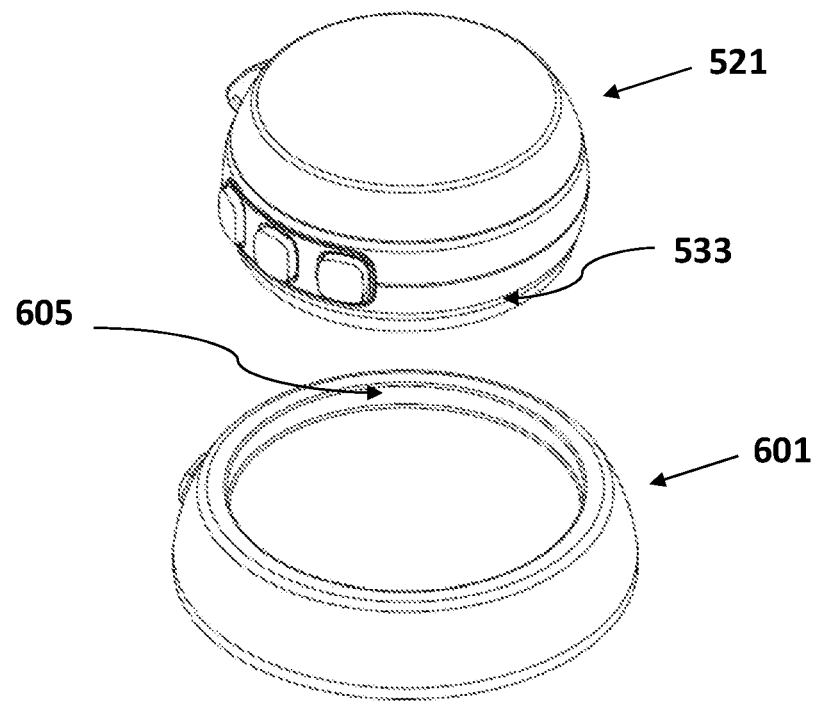
FIG. 13 is an elevated perspective view of the medical device depicted in FIG. 9 (without adaptor) and a second wireless charger.

FIGS. 12 and 13 depict a first wireless charger 600 and a second wireless charger 601. The medical device 521 can fit side on in the first wireless charger 600, which arrangement permits the device to be charged with an adaptor (here, the otoscope adaptor, 650) engaged to the base. The first wireless charger 600 includes three holders 303, 610 and 620: the first holder 303 receives a slit beam pen 301; a second holder 610 receives a fundosccope adaptor 630; and a third other 620 holder receives a dermascope adaptor 640.

The medical device 521 includes a charging ring 533 which engages with a complementary shaped charging ring 605 in the wireless chargers 600 and 601 (the complementary shaped charging ring is not shown in the wireless charger 600 of FIG. 12).

A medical device 521 with a dermascope adaptor 640 is depicted FIGS. 14 and 15. In FIG. 15, the device is depicted in use inspecting the skin of a patient 800. The adaptor 640 is lockingly engaged with the base 520 in FIG. 15. As can be seen in this figure, the medical device provides display 570 that is located adjacent to the opening 525 in the base 520, and a patient is directly viewable through the opening 525 of the medical device. The medical device 521 provides for a first (direct) inspection of the patient 800 through the opening 525, and for a contemporaneous second inspection of the patient 800 by inspection of the images of the patient captured by the image capturing 541 device and displayed on the display 570.

The device 521 and dermascope adaptor 640 is able to be handled by the peripheral portion 531. In particular, the device 521 is able to be handled by the thumb and one finger of the hand 900 of a person inspecting the patient. Alternatively, the device is able to be handled by the strut 527 (not shown).

A medical device 521 with an otoscope adaptor 650 and reusable sheath 654A is depicted FIG. 16A, and FIG. 17. In FIG. 16B the otoscope adaptor is separately depicted from a rear perspective. In FIGS. 16A and 16B the open otoscope adaptor has four apertures 655 (only one of which is indicated by a reference numeral) in the body of the adaptor 650, where the one or more apertures 655 permit the removal of objects within the adaptor. The otoscope adaptor has a domed lower portion 657 and includes a projecting portion 652 in the shape of a funnel (frusto-conical in shape).

The projecting portion 652 is located in the central axis of the lower portion of the otoscope adaptor 650 (when viewed in plan view from directly above), and it narrows as it extends outwardly from the lower portion 657. The projecting portion 652 includes an aperture 656 which extends from an upper part 659 of the projecting portion to a lower part 658 of the projecting portion. The aperture 656 in the projecting portion 652 extends into and forms a continuous aperture with one of the apertures 655 in the lower portion of the adaptor 650.

The apertures 655 are defined by a plurality adaptor struts 651 (just one of which is indicated by a reference numeral) which extend from a peripheral portion of the adaptor to the lower portion 657 of the projecting portion 652 of the adaptor. The plurality of struts 651 provide structural support to the adaptor 650 so that pressure which the adaptor receives during normal use does not damage the form of the adaptor 650.

In FIG. 17, the device is depicted in use inspecting the ear of a patient 810. The adaptor 650 is lockingly engaged with the base in FIG. 17. As can be seen in this figure, the medical device provides display 570 that is located adjacent to the opening 525 in the base, and the patient's ear 810 is directly viewable and/or accessible through the opening 525 of the medical device 521. The medical device 521 provides for a first (direct) inspection of the patient's ear 810 through the opening 525 and the otoscope adaptor 650, and for a contemporaneous second inspection of the patient's ear 810 by inspection of the images of the patient captured by the image capturing 541 device and displayed on the display 570.

The apertures 655 in the adaptor are shaped such that in use, they permit the user of the device to remove debris from the ear of the patient 810. The speculum sheath 654A (not visible in FIG. 17) is mounted to the otoscope adaptor 650. Returning to FIG. 16A, the projecting portion 652 of the adaptor 650 includes mounting means to mount a speculum sheath, the mounting means comprising a form fitting arrangement such that the projecting portion of the adaptor 652 includes a mounting element (not shown) having a complementary shape to a mounting element 654 on the speculum sheath 654A. The mounting element 654 on the adaptor is a furrowed strip extending around an external part of the projecting portion 652. The complementary shaped mounting element (not shown) on the speculum sheath 654A is a protruding strip which extends around an internal part of sheath, such that the speculum sheath 654A is mountable by twisting the sheath on the projecting portion 652 such that the two complementary mounting elements become engaged. A branded speculum sheath (e.g. Welch Allyn) having a mounted element (not shown) can be mounded on the projecting portion 652 in a similar fashion.

The device 521 including the otoscope adaptor 650 is able to be handled by the peripheral portion 531. In particular, the device 521 is able to be handled by the thumb and one finger of the hand 900 of a person inspecting the patient. Alternatively, the device is able to be handled by the strut 527 (not shown).

Figure 18:
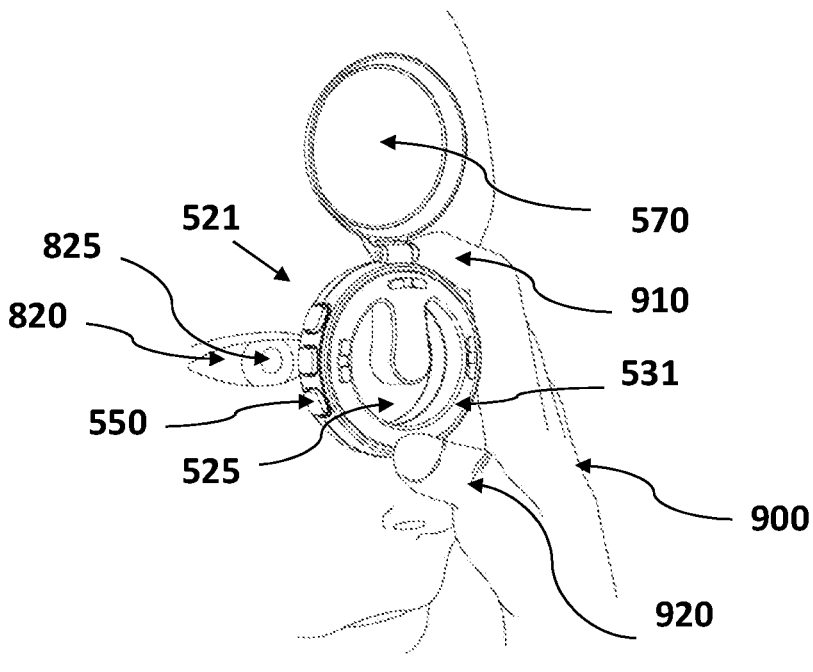
FIG. 18 is a front perspective view of the medical device depicted in FIG. 9, in use as an ophthalmoscope (without any adaptor).

A medical device 521 with is depicted in use in FIG. 18 as an ophthalmoscope without any adaptor. In FIG. 18, the device is depicted in use inspecting the eye of a patient 820. The device 521 in this application is intended to be used together with an externally provided slit beam, such as the slit beam pen 300 depicted in FIGS. 6A and 6B. As can be seen in this figure, the medical device provides display 570 that is located adjacent to the opening 525 in the base, and a patient's eye 820 is directly viewable and/or accessible through the opening 525 of the medical device. The medical device 521 provides for a first (direct) inspection of the patient's eye 820 through the opening 525, and for a contemporaneous second inspection of the patient's eye 820 by inspection of the images of the patient captured by the image capturing 541 device and displayed on the display 570.

The device 521 is able to be handled by the peripheral portion 531. In particular, the device 521 is able to be handled by the thumb 920 and one finger 910 of the hand 900 of a person inspecting the patient. Alternatively, the device is able to be handled by the strut 527 (not shown).

Figure 19:
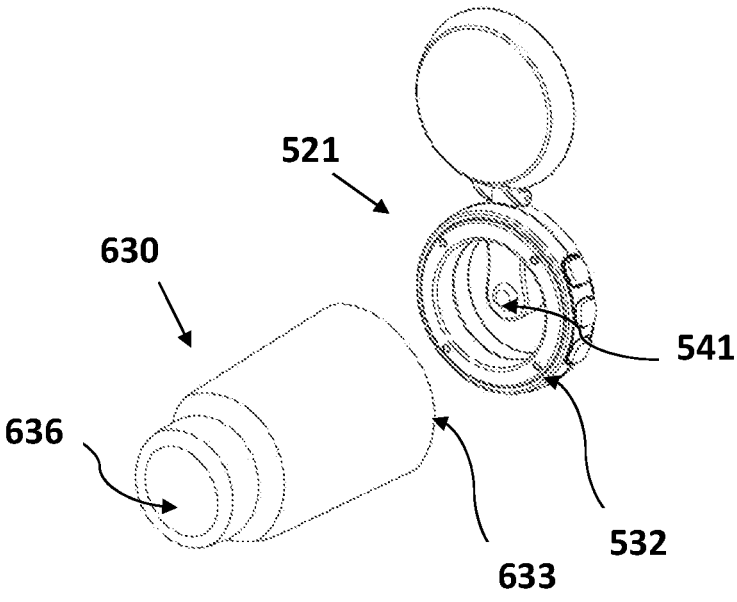
FIG. 19 is a front perspective view of the medical device depicted in FIG. 9 and a separate fundoscope adaptor.
Figure 20:
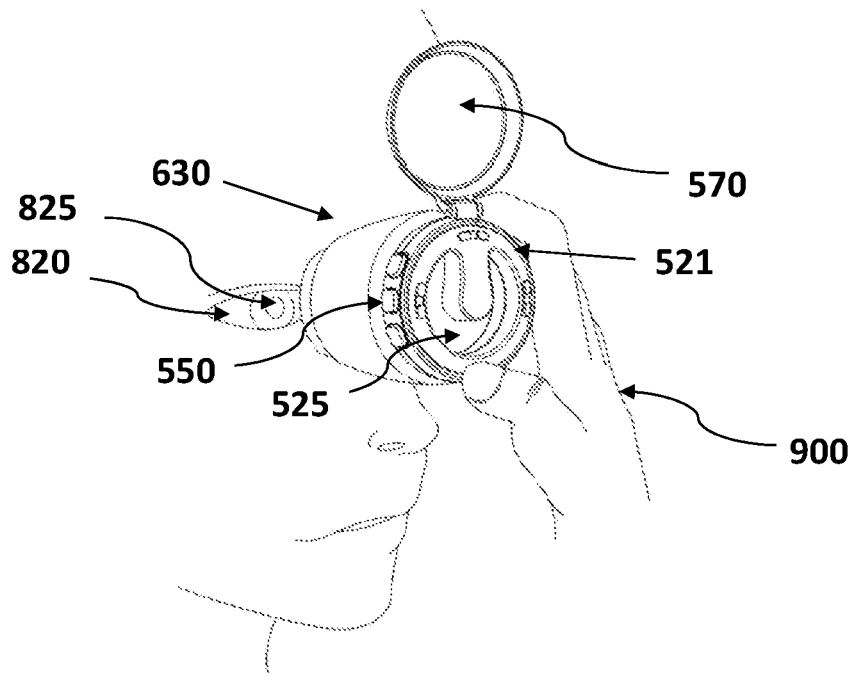
FIG. 20 is a front perspective view of the medical device depicted in FIG. 9, and the fundosccope adaptor depicted in FIG. 19, in use.

A medical device 521 with a fundosccope adaptor 630 is depicted FIGS. 19 and 20. In FIG. 20, the device is depicted in use inspecting the fundus of the eye of a patient 820. The adaptor 630 is lockingly engaged with the base 520 in FIG. 20. As can be seen in this figure, the medical device provides a display 570 that is located adjacent to the opening 525 in the base, and the patient's eye 820 (or the region around the eye) is directly viewable through the opening 525 of the medical device 521 and through the fundosccope adaptor 630. The medical device 521 provides for a first (direct) inspection of the patient's eye 820 (or the region around the eye) or fundus through the opening 525 and the fundosccope adaptor 630, and for a contemporaneous second inspection of the patient's eye 820 by inspection of the images of the patient captured by the image capturing 541 device and displayed on the display 570.

The device 521 and fundosccope adaptor 630 is able to be handled by the peripheral portion 531. In particular, the device 521 is able to be handled by the thumb and one finger of the hand 900 of a person inspecting the patient. Alternatively, the device is able to be handled by the strut 527 (not shown). FIG. 20 depicts a medical device 521 lockingly engaged with the fundosccope adaptor 630, which is broadly frustoconical in shape. The fundosccope adaptor 630 includes a fundus lens 636 that, when the adaptor is connected to the base of the device, aligns with at least one image capturing device on the base of the device. The fundus lens 636 assists with imaging the fundus at the rear of the patient's eye 820. The adaptor 630 includes light direction means (also not shown) that, when aligned with at least one of the light sources on the base of the device, directs light into the pupil of the eye 825.

In use, the image capturing device (not shown) is aligned with the pupil 825 of the patient, and the adaptor 630 (engaged with the device 521) is placed in close proximity to the eye (approximately 3-5 centimetres), so that the image capturing device 541 is located a distance of (approximately 5-8 centimetres) away from the pupil 825. In this configuration, the fundosccope produces an image of the fundus that is captured by the image capturing device, and that image is displayed on the display 570. The light emitted by the light sources on the base of the device are transmitted by light transmission means (not shown) and directed to a central axis which is aligned with the central axis of the fundus lens.

The image capturing device 541 is able to automatically-focus the image of the fundus provided by the lens 636 so that the captured image is a focussed image of the fundus of a patient. The automatic focussing is performed by the image capturing device 541 (together with the software controlling same) detecting distance between the eye of the patient 820 and the image capturing device, the alignment of the camera with the central part of the pupil of the eye 820, and analysing image quality parameters, to adjust the digital or optical focus and/or apply digital image processing to improve the image.

Alternatively, or in combination with aforementioned automatic focussing and image quality improvement, the image captured by the image capturing device 541 is focussed using by manual control of the control buttons 550 on the surface of the device 521.

Alternatively (not shown), the captured image may be displayed on a remotely located screen (e.g. the display of a tablet or a personal computer of the medical practitioner). In this application, it is not necessary for the medial practitioner (in particular, the face of the medical practitioner) to be in close proximity to the patient, as they can inspect the fundus of the patient by the remotely located screen. This provides a more comfortable examination for the patient. The medical practitioner can use the headband 450 to position the device the in the appropriate location for inspecting the fundus, and operate the device 521 (e.g. focus or move the camera) via remotely located controls (not shown) that communicate wirelessly with the medical device.

The device 521 and adaptor 630 are shaped so that the outer surface of the device and fundosccope adaptor are together manoeuvrable for examination of the fundus without contacting the patient (e.g. the patient's nose).

Figure 21:
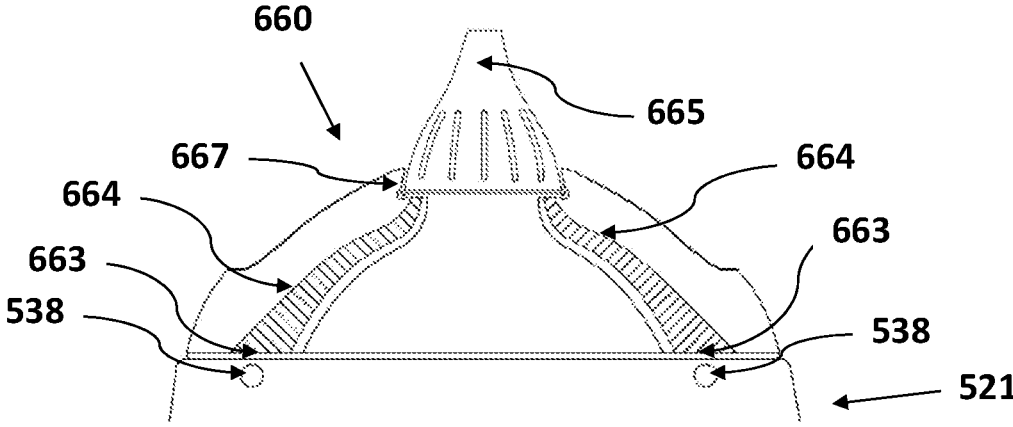
FIG. 21 is a side transparent view of the fundosccope adaptor depicted in FIG. 20, a schematic of a patient's eye and the medical device depicted in FIG. 9.
Figure 22:
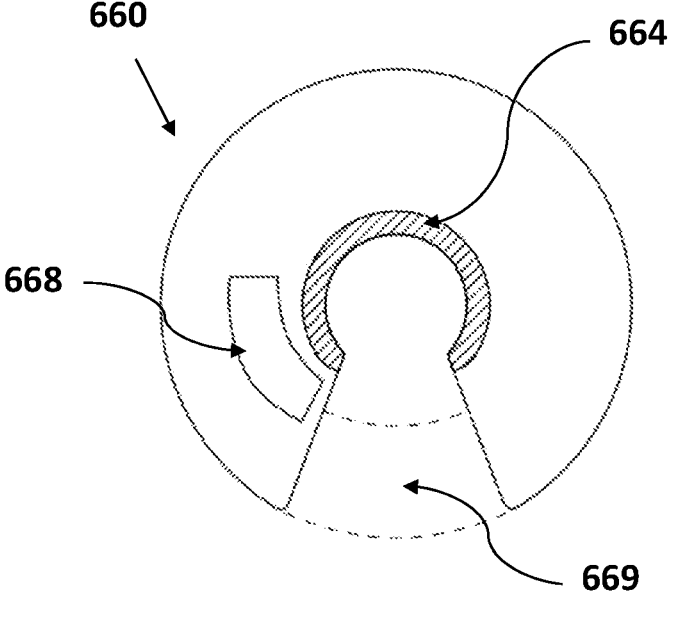
FIG. 22 is a top plan view of the otoscope adaptor depicted in FIG. 22.

FIGS. 21 and 22 depict a second otoscope adaptor 660 able to receive a reusable speculum 665. The otoscope adaptor 660 is domed in shape, and includes a speculum receiving portion 667 and a cut-out section 669 in the adaptor. The speculum receiving portion 667 is located towards an upper part of the adaptor. The speculum receiving portion 667 is shaped to receive and hold a lower part of the reusable speculum 665. The adaptor 660 includes securing means comprising a sliding tab 668 to secure the speculum 665 in place once it is received into the speculum receiving portion 667. The adaptor 660 includes a cut-out section 669 extending from an upper portion of the adaptor to a lower portion of the adaptor, through which the reusable speculum 665 can be placed to be received in the speculum receiving portion 667. The lower portion of the adaptor 660 is adapted to lockingly engage with the base of the medical device 521 via engagement of the engaging rim 633 of the adaptor with the outer ring 532 of the device comprising a frictional connecting ridged surface.

The adaptor 660 includes light transmission means comprising fibre options 664 to transmit light from the light sources 538 along a length of the adaptor 660, such that light is transmitted from a lower portion of the adaptor to an upper portion of the adaptor and into the speculum 665 for illuminating the ear of the patient. The light transmission means optically connects with the light sources 538 to transmit the light therefrom to the upper portion of the adaptor 660 and speculum 665.

The second otoscope adaptor 660 is for use with a reusable speculum 665. The reusable speculum 665 is made of stainless steel and adapted to be sterilised.

Figure 23:
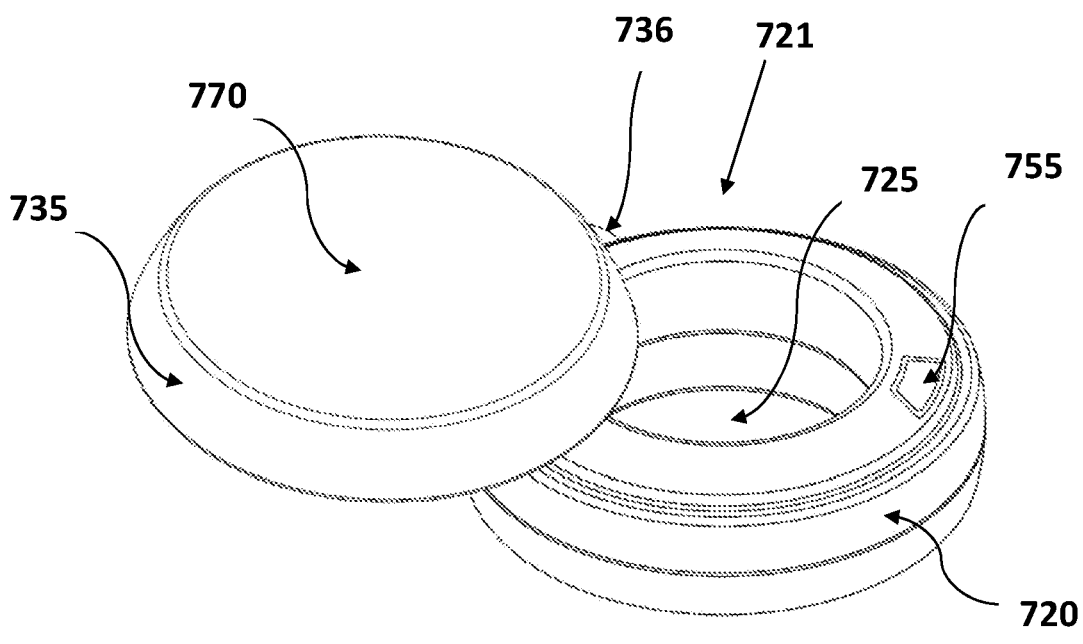
FIG. 23 is a top perspective view of the medical device according to a third preferred embodiment of the present invention.
Figure 24:
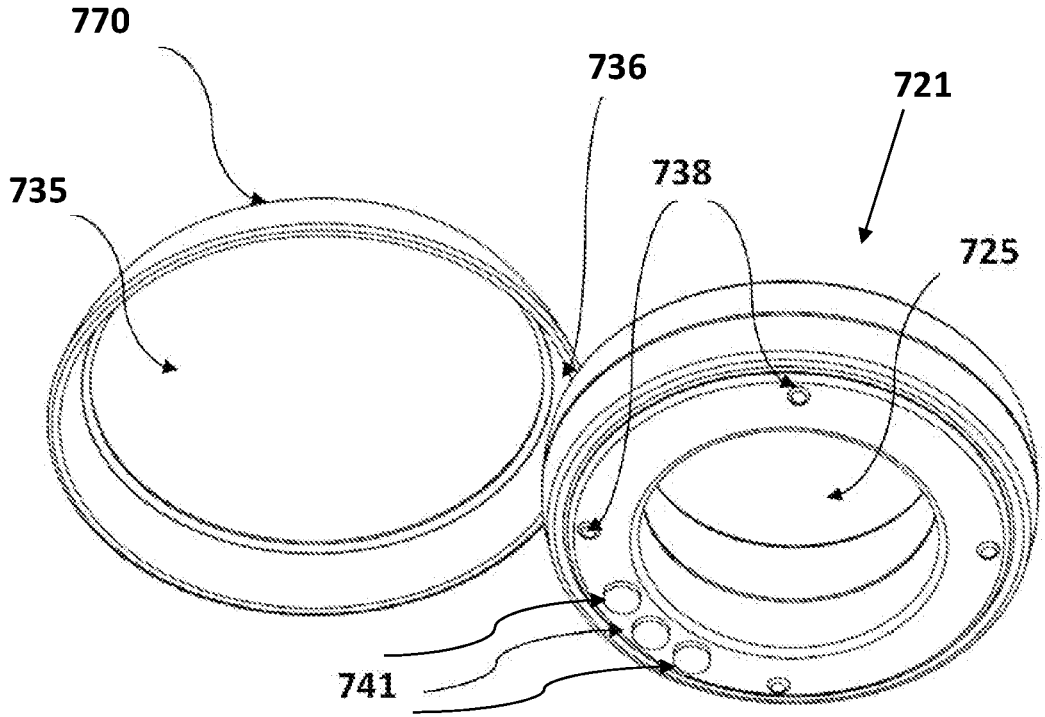
FIG. 24 is a bottom perspective view of the medical device depicted in FIG. 24.

FIGS. 23 and 24 depict a fourth preferred embodiment of a medical device 721. The device includes a lid 735 which can be moved with respect to the base 720 by sliding about a sliding joint 736 (c.f. the pivoting lid of medical device 521 depicted in FIGS. 8 to 11). The display 770 is located on the outer surface of the lid 735. The device includes a circular (in plan view) opening 725 which is located adjacent to the cameras 741.

The image capturing device includes three cameras 741 which co-operate so as to provide a monochrome mode for increased dynamic range of regular shots (compared to a single camera) by combining the data from standard RGB and light-sensitive black and white sensors. The plurality of cameras 741 include hybrid zoom technology which combines data from the three cameras to produce higher resolution images for a better quality zoom (compared to a single camera). A high-quality depth of field effect is also provided through both software emulation and the use of multiple focal lengths in the three cameras 741.

The three cameras are each be able to rotate, swivel, turn or otherwise be moved with respect to the base 520 of the device 721. The movement of the image capturing device(s) may preferably be controlled by a user operating the touch-pad 755 or touchscreen 770 located on the device. The device 721 further includes a microphone (not shown) for voice activated control, and a speaker, whereby the microphone and speaker provide for live streaming of a medical inspection and/or operation and communication with other medical practitioner(s) via the internet.

The medical device 721 is able to engage with one or more adaptors, and be used, in the same manner as the third preferred embodiment 521.

The device 721 includes data storage means (not shown) to store the images captured by the image capturing device 741 on the device itself. The data storage means is a digital machine readable medium comprising an encrypted flash drive capable of receiving data from, and storing in a digitally readable format the images captured by, the image capturing device 741. The device includes wireless communication means (not shown) to wirelessly communicate images captured by the image capturing device 741 to the display 770 via Bluetooth short-range wireless communication. The device is also able to use the wireless communication means to communicate said captured images to the medical practitioner's computer enabled to connect using Bluetooth communication (not shown) and via Wi-Fi to a computer or server of the institution in which the medical practitioner provides medical treatment. The wireless communications means is also able to communicate the images captured by the image capturing device 741 to an external display (not shown). The wirelessly communicated images are contemporaneously provided to the medical practitioner performing the inspection or operation (or other medical practitioners, with the consent of the patient) for viewing without recording those images in a format that can later be reproduced. Alternatively, the images may be communicated in a manner for viewing which enables recording of the images.

The display 770 shows settings of the image capturing device 741 in in addition to the captured image. The display 770 is a touchscreen, which includes the ability to both present the images captured by the image capturing device 741, as well as provide other controls or functions for the user of the device 721. Another control of the device is a touchpad 755 located on the upper surface of the base 720 of the device.

Operation

In use a medical practitioner user of the medical device 11, 111, 211, 521, 721 can hold the outer surface of the peripheral portion 21, 121, 221, 531, 731 of the base 20, 120, 220, 520, 720 to locate the device 11, 111, 211, 521, 721 over the particular portion of the patient's body being inspected or accessed. However even though the medical device is over the particular portion of the patient's body being inspected a physical immediate review can be undertaken by the practitioner by looking through the open channel formed by the aligned open areas 25, 35, 125, 225, 525, 725 as close as possible to the view by the image capturing device 41, 541, 741 and with the same illumination as the image capturing device 41, 541, 741. Generally, the medical device can be held at a distance from the patient's body or a spacer is built into the device to provide a correct focal point of the camera at the required surface of the body. A speculum can be used to provide this spacing while also eliminating external optical interferences.

It can be seen that the practitioner has a better ability to locate the medical device at the required location of the patient's body without having fingers in the way.

The practitioner also has a better ability to pre-inspect the patient by viewing through the aligned open areas 25, 35, 125, 225, 525, 725 without substantial hindrance and as close as possible to the view by the image capturing device 41, 541, 741 and with the same illumination as the image capturing device 41, 541, 741.

The practitioner has a better ability to focus and align the camera 41, 541, 741 and to know what image is being obtained by the camera and how that image correlates with the pre-inspected direct viewing through the open channel formed by the aligned open areas 25, 35, 125, 225, 525, 725 as close as possible to the view by the image capturing device 41, 541, 741 and with the same illumination as the image capturing device 41, 541, 741.

Further the practitioner is able to use the same medical device with different attachments or adaptors to form different enhanced versions of optically enabled medical inspection or operation.

The practitioner is able to extend the scope of medical services provided without the need to have a plurality of standalone separate devices for medical inspection, operation or procedural use.

The practitioner is able to operate in an improved manner by having the images recorded and stored for review or comparative purposes, or to enable the more ready sharing of the images (together with medical commentary at the practitioner's option) with others involved in the provision of medical advice to the patient the subject of the images. Such improvements in the documentation and communication of medical records are considered to provide substantial assistance in a telehealth context, in particular, and it is envisaged that the medical device the subject of this invention may co-operate with a number of other electronically enabled medical devices to further enhance the foregoing benefits in the provision of healthcare to the patient and the practice of the medical practitioner alike. In particular, the device may be co-operable in with other wired or preferably wireless medical instruments such as a stethoscope, thermometer, pulse oximeter or spirometer, where the data recorded by a number of such devices is recorded to and accessible via a centrally connected database.

GENERAL STATEMENTS

It will be appreciated by those skilled in the art that many modifications and variations may be made to the embodiments described herein without departing from the spirit and scope of the invention.

Throughout the specification and claims, the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features, that it directly references, but also other components, steps or features not specifically listed, unless the contrary is expressly stated or the context requires otherwise.

In the present specification, terms such as "part", "component", "means", "section", or "segment" may refer to singular or plural items and are terms intended to refer to a set of properties, functions or characteristics performed by one or more items having one or more parts. It is envisaged that where a "part", "component", "means", "section", "segment", or similar term is described as consisting of a single item, then a functionally equivalent object consisting of multiple items is considered to fall within the scope of the term; and similarly, where a "part", "component", "means", "section", "segment", or similar term is described as consisting of multiple items, a functionally equivalent object consisting of a single item is considered to fall within the scope of the term. The intended interpretation of such terms described in this paragraph should apply unless the contrary is expressly stated or the context requires otherwise.

The term "connected" or a similar term, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means. "Connected", or a similar term, may mean that two or more elements are either in direct physical or electrical contact, or that two or more elements are not in direct contact with each other yet still co-operate or interact with each other.

The dimensions provided in relation to the illustrative device are not intended to be prescriptive of all device falling within the scope of the invention. The dimensions are provided for illustrative purposes only and should not be construed otherwise.

The mere disclosure of a product or method element in the specification should not be construed as being essential to the invention claimed herein, except where it is either expressly stated to be so or expressly recited in a claim.

The terms in the claims have the broadest scope of meaning they would have been given by a person of ordinary skill in the art as of the relevant date.

The terms "a" and "an" mean "one or more", unless expressly specified otherwise.

Neither the title nor any abstract of the present application should be taken as limiting in any way the scope of the claimed invention.

Where the preamble of a claim recites a purpose, benefit or possible use of the claimed invention, it does not limit the claimed invention to having only that purpose, benefit or possible use.

While there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the medical industries.

The invention claimed is:

1. A medical device for inspecting a patient, the device including:
    a hand-holdable base having a central axis and defining a planar surface perpendicular to the central axis wherein the base comprises a length along the central axis which is less than a width along the planar surface, wherein the hand-holdable base comprises a disk;
    the base comprising a camera structured for capturing images of the patient, the camera being located in the base along the central axis; and
    circuitry to communicate the captured images to a display configured for displaying said captured images,
    wherein the base includes one or more openings configured and dimensioned to enable the patient to be directly inspected through the one or more openings, the base further includes a peripheral portion, the one or more openings being located between the camera and the peripheral portion and the one or more openings surround, or substantially surround the camera, the one or more openings comprising a crescent-shaped opening through the base on three sides of the camera, wherein the width of the planar surface of the base comprises a diameter of the disk part of which spans the at least one opening.

2. A medical device according to claim 1, wherein the camera is embedded in the base.

3. A medical device according to claim 2, wherein the medical device includes a display located adjacent to the one or more openings.

4. A medical device according to claim 3, wherein the device provides for a first inspection and a second contemporaneous inspection of a patient, whereby the first inspection is by direct inspection of the patient through the one or more openings, and the second inspection is by inspection of the images of the patient captured by the camera and displayed on the display.

5. A medical device according to claim 1, wherein the device includes one or more struts to locate the camera relative to the peripheral portion.

6. A medical device according to claim 5, wherein the one or more struts extend inwardly from the peripheral portion to the camera.

7. A medical device according to claim 5, wherein the camera is located within a first a plane defined by an upper surface of the peripheral portion, and a second plane defined by a lower surface of the peripheral portion.

8. A medical device according to claim 5, wherein the device includes one or more struts that extend upwardly from the peripheral portion of the base to locate the camera in an area above the one or more openings.

9. A medical device according to claim 5, wherein the peripheral portion is ring shaped.

10. A medical device according to claim 4, wherein the display is located on the device.

11. A medical device according to claim 10, wherein the display is located on a lid of the device.

12. A medical device according to claim 11, wherein the lid is moveable relative to the base of the device from an open position to a closed position, and when the lid is in the open position, the patient is directly viewable or accessible through the medical device.

13. A medical device according to claim 1, wherein the device is configured for performing operations and/or procedures on the patient using tools inserted through the one or more openings of the base without the operations and/or procedures obstructing the images captured by the camera.

14. A medical device according to claim 1, wherein the base is able to lockingly engage with one or more adaptors so the device may be used as one or more of the following:

a. an otoscope;
b. an ophthalmoscope;
c. a fundosccope;
d. a dermatoscope.

15. A medical device according to claim 1, wherein the base is able to lockingly engage with one or more adaptors so the device may be used as one or more of the following:

a. an endoscope;
b. a laryngoscope; and/or
c a colonoscope.

16. A medical device according to claim 1 wherein the device includes, and is able to lockingly engage with, an otoscope adaptor to allow performance of an operation or procedure through the otoscope adaptor.

17. A medical device according to claim 16 wherein the otoscope adaptor includes one or more apertures to permit removal of objects within the adaptor.

18. A medical device according to claim 1, wherein the device includes, and is able to engage with an otoscope adaptor adapted to transmit light from an at least one light source of the device along a length of the otoscope adaptor for illumination of the patient.

19. A medical device in accordance with claim 1, wherein the device includes, and is able to engage with, an otoscope adaptor adapted for use with reusable and/or disposable specula or speculum sheaths.

20. The medical device of claim 1, wherein the one or more openings is sized and configured to allow a manipulable tool to be inserted through the one or more openings to interact with a surface of the patient and for a user to be able to manipulate the manipulable tool inserted through the one or more openings to conduct a procedure or operation on the surface of the patient.

21. A handheld medical device comprising:

a hand-holdable base having a length extending along a central axis and defining a planar surface perpendicular to the central axis, the planar surface having a width, the length of the base extending along the central axis being less than the width of the planar surface, the hand-holdable base comprising a disk;

a camera disposed in the base along the central axis; and an electronic display connected to the camera, wherein the base defines at least one opening therethrough, the at least one opening being configured and dimensioned to enable direct inspection and tool access therethrough, the base further including a peripheral portion, the at least one opening being located between the camera and the peripheral portion, the at least one opening surrounding, or substantially surrounding, the camera, the at least one opening comprising a crescent-shaped opening through the base on three sides of the camera, wherein the width of the planar surface of the base comprises a diameter of the disk part of which spans the at least one opening.

22. The handheld medical device of claim 21 wherein the electronic display is disposed inside a flip-up lid attached to the base, the flip-up lid in an open position exposing both the crescent-shaped opening and a display surface of the electronic display, the flip-up lid in a closed position covering the crescent-shaped opening and protecting and hiding the display surface of the electronic display.

* * * * *